(12) United States Patent
Deshpande

(10) Patent No.: US 10,040,922 B2
(45) Date of Patent: Aug. 7, 2018

(54) OXYGEN SCAVENGERS, COMPOSITIONS COMPRISING THE SCAVENGERS, AND ARTICLES MADE FROM THE COMPOSITIONS

(71) Applicant: Girish N. Deshpande, Morris Plains, NJ (US)

(72) Inventor: Girish N. Deshpande, Morris Plains, NJ (US)

(73) Assignee: PLASTIPAK PACKAGING, INC., Plymouth, MI (US)

( * ) Notice: Subject to any disclaimer, the term of this patent is extended or adjusted under 35 U.S.C. 154(b) by 0 days.

(21) Appl. No.: 14/935,953

(22) Filed: Nov. 9, 2015

(65) Prior Publication Data

US 2016/0229988 A1 Aug. 11, 2016

Related U.S. Application Data

(63) Continuation of application No. 12/945,351, filed on Nov. 12, 2010, now Pat. No. 9,181,414.

(60) Provisional application No. 61/261,158, filed on Nov. 13, 2009.

(51) Int. Cl.
| | | |
|---|---|---|
| *C08K 5/3417* | (2006.01) | |
| *C07D 209/46* | (2006.01) | |
| *C08K 5/00* | (2006.01) | |
| *C08K 5/098* | (2006.01) | |
| *B65D 1/02* | (2006.01) | |
| *B65D 81/26* | (2006.01) | |
| *C08L 67/00* | (2006.01) | |

(52) U.S. Cl.
CPC .......... *C08K 5/3417* (2013.01); *B65D 1/0207* (2013.01); *B65D 81/266* (2013.01); *C07D 209/46* (2013.01); *C08K 5/0083* (2013.01); *C08K 5/098* (2013.01); *C08K 2201/012* (2013.01); *C08L 67/00* (2013.01)

(58) Field of Classification Search
CPC ... C08K 5/3417; C09D 209/00; C09D 209/46
See application file for complete search history.

(56) References Cited

U.S. PATENT DOCUMENTS

| | | | | |
|---|---|---|---|---|
| 2,841,591 | A * | 7/1958 | Prichard | C07D 209/46 548/460 |
| 3,317,558 | A * | 5/1967 | Becke | C07D 209/46 548/472 |
| 3,322,785 | A * | 5/1967 | Fletcher | B01D 53/46 210/749 |
| 4,536,409 | A | 8/1985 | Farrell et al. | |

(Continued)

FOREIGN PATENT DOCUMENTS

| | | |
|---|---|---|
| AR | P080102003 | 5/2008 |
| AU | 2008251476 | 5/2008 |

(Continued)

OTHER PUBLICATIONS

U.S. Appl. No. 12/117,849 (U.S. Pat. No. 7,994,245), filed May 9, 2008 (Aug. 9, 2011), Deshpande et al.

(Continued)

*Primary Examiner* — Brieann R Johnston
(74) *Attorney, Agent, or Firm* — Ballard Spahr, LLP

(57) ABSTRACT

The present disclosure relates to oxygen scavenging molecules, compositions comprising the molecules, and articles made from the compositions.

20 Claims, 2 Drawing Sheets

(56) References Cited

U.S. PATENT DOCUMENTS

| | | |
|---|---|---|
| 4,786,671 A | 11/1988 | Kress et al. |
| 5,021,515 A | 6/1991 | Cochran et al. |
| 5,049,624 A | 9/1991 | Adams et al. |
| 5,075,362 A | 12/1991 | Hofeldt et al. |
| 5,116,547 A | 5/1992 | Tsukahara et al. |
| 5,211,875 A | 5/1993 | Speer et al. |
| 5,250,592 A | 10/1993 | Nesvadba |
| 5,639,815 A | 6/1997 | Cochran et al. |
| 5,955,527 A | 9/1999 | Cochran et al. |
| 6,610,234 B2 | 8/2003 | Akkapeddi et al. |
| 6,780,916 B2 | 8/2004 | Tung et al. |
| 7,691,290 B2 | 4/2010 | Deshpande et al. |
| 7,879,930 B2 | 2/2011 | Liu |
| 7,994,245 B2 | 8/2011 | Deshpande et al. |
| 8,431,721 B2 | 4/2013 | Deshpande et al. |
| 8,450,398 B2 | 5/2013 | Deshpande |
| 8,721,920 B2 | 5/2014 | Deshpande et al. |
| 8,748,519 B2 | 6/2014 | Deshpande |
| 8,975,345 B2 | 3/2015 | Deshpande |
| 9,181,414 B2 | 11/2015 | Deshpande |
| 9,222,020 B2 | 12/2015 | Deshpande |
| 9,475,630 B2 | 10/2016 | Deshpande et al. |
| 2003/0109643 A1 | 6/2003 | Ching et al. |
| 2004/0241468 A1 | 12/2004 | Otaki |
| 2006/0069197 A1 | 3/2006 | Tammaji et al. |
| 2006/0180790 A1 | 8/2006 | Deshpande et al. |
| 2006/0182911 A1 | 8/2006 | Tammaji et al. |
| 2006/0247388 A1 | 11/2006 | Hale et al. |
| 2007/0066731 A1 | 3/2007 | Tattum et al. |
| 2007/0241309 A1 | 10/2007 | Uradnisheck |
| 2008/0161472 A1 | 7/2008 | Jenkins et al. |
| 2008/0255280 A1 | 10/2008 | Sims et al. |
| 2008/0277622 A1 | 11/2008 | Deshpande et al. |
| 2009/0030115 A1 | 1/2009 | Liu |
| 2009/0278087 A1 | 11/2009 | Deshpande et al. |
| 2010/0154361 A1 | 6/2010 | Deshpande et al. |
| 2011/0171405 A1 | 7/2011 | Deshpande |
| 2011/0172335 A1 | 7/2011 | Deshpande |
| 2011/0251395 A1 | 10/2011 | Deshpande et al. |
| 2011/0275750 A1 | 11/2011 | Bene et al. |
| 2012/0175555 A1 | 7/2012 | Menozzi et al. |
| 2012/0199515 A1 | 8/2012 | Peters et al. |
| 2012/0283366 A1 | 11/2012 | Akkapeddi et al. |
| 2013/0158182 A1 | 6/2013 | Menozzi et al. |

FOREIGN PATENT DOCUMENTS

| | | |
|---|---|---|
| AU | 2008251476 A1 | 11/2008 |
| AU | 2010303748 | 9/2010 |
| AU | 2010319298 | 11/2010 |
| AU | 2010319302 | 11/2010 |
| AU | 2010319384 | 11/2010 |
| AU | 2014224080 | 9/2014 |
| BR | PI0810744-0 | 5/2008 |
| CA | 1272341 A1 | 7/1990 |
| CA | 2247985 A1 | 9/1997 |
| CA | 2687081 | 5/2008 |
| CA | 2779714 | 9/2010 |
| CA | 2780746 | 11/2010 |
| CA | 2780749 | 11/2010 |
| CA | 2780768 | 11/2010 |
| CL | 1391/2008 | 5/2008 |
| CN | 101072820 A | 11/2007 |
| CN | 200880023116.X | 5/2008 |
| CN | 101193976 A | 6/2008 |
| CN | 101688020 A | 3/2010 |
| CN | 2013106426272 | 12/2013 |
| DE | 134980 C | 6/1901 |
| DE | 442774 C | 4/1927 |
| EP | 0144 807 A2 | 6/1985 |
| EP | 08795847.6 | 5/2008 |
| EP | 10822439.5 | 9/2010 |
| EP | 10830816.4 | 11/2010 |
| EP | 10830818.0 | 11/2010 |
| EP | 10830821.4 | 11/2010 |
| EP | 2483342 A2 | 8/2012 |
| EP | 14150235.1 | 1/2014 |
| GB | 1490671 A | 11/1977 |
| HK | 10107172.3 | 7/2010 |
| IN | 7423/DELNP/2009 | 5/2008 |
| JP | H01-026667 A | 1/1989 |
| JP | 2010-507697 | 5/2008 |
| JP | 2013-105954 | 5/2013 |
| KR | 10-2009-7025208 | 5/2008 |
| MX | MX/a/2009/012183 | 5/2008 |
| MX | MX/a/2013/001496 | 2/2013 |
| RU | 2307846 C2 | 10/2007 |
| RU | 2009145713 | 5/2008 |
| RU | 2406741 C2 | 12/2010 |
| RU | 2009145713 A | 6/2011 |
| RU | 2013142425 | 9/2013 |
| TW | 097117502 | 5/2008 |
| TW | 103123705 | 7/2014 |
| VE | 2008-000929 | 5/2008 |
| WO | WO-1995/02616 A2 | 1/1995 |
| WO | WO-199502616 A2 | 1/1995 |
| WO | WO-2003/109643 | 6/2003 |
| WO | WO-2004/063247 A1 | 7/2004 |
| WO | WO-2005073272 A1 | 8/2005 |
| WO | WO-2006/062816 A2 | 6/2006 |
| WO | WO-2006/088889 A2 | 8/2006 |
| WO | PCT/US2008/063250 | 5/2008 |
| WO | WO-2008/141185 A1 | 11/2008 |
| WO | WO-2009/152114 A1 | 12/2009 |
| WO | PCT/US2010/050719 | 9/2010 |
| WO | PCT/US2010/056585 | 11/2010 |
| WO | PCT/US2010/056594 | 11/2010 |
| WO | PCT/US2010/056598 | 11/2010 |
| ZA | 2009/08083 | 5/2008 |

OTHER PUBLICATIONS

U.S. Appl. No. 13/164,447 (U.S. Pat. No. 8,431,721), filed Jun. 20, 2011 (Apr. 30, 2013), Deshpande et al.
U.S. Appl. No. 13/849,797 (U.S. Pat. No. 9,475,630), filed Mar. 25, 2013 (Oct. 25, 2016), Deshpande et al.
U.S. Appl. No. 15/147,532, filed May 5, 2016, Deshpande et al.
U.S. Appl. No. 61/246,956, filed Sep. 29, 2009, Deshpande.
U.S. Appl. No. 12/893,817 (US 2011/0123741), filed Sep. 29, 2010 (May 26, 2011), Deshpande.
U.S. Appl. No. 61/261,158, filed Nov. 13, 2009, Deshpande.
U.S. Appl. No. 12/945,351 (U.S. Pat. No. 9,181,414), filed Nov. 12, 2010 (Nov. 10, 2015), Deshpande.
U.S. Appl. No. 61/261,209, filed Nov. 13, 2009, Deshpande.
U.S. Appl. No. 12/945,353 (U.S. Pat. No. 8,478,519), filed Nov. 12, 2010 (Jun. 10, 2014), Deshpande.
U.S. Appl. No. 14/258,823 (U.S. Pat. No. 8,975,345), filed Apr. 22, 2014 (Mar. 10, 2015), Deshpande.
U.S. Appl. No. 14/585,413, filed Dec. 30, 2014, Deshpande.
U.S. Appl. No. 61/261,219, filed Nov. 13, 2009, Deshpande.
U.S. Appl. No. 12/945,355 (U.S. Pat. No. 8,450,398), filed Nov. 12, 2010 (May 28, 2013), Deshpande.
U.S. Appl. No. 13/889,133 (U.S. Pat. No. 9,222,020), filed May 7, 2013 (Dec. 29, 2015), Deshpande.
U.S. Appl. No. 14/976,766, filed Dec. 21, 2015, Deshpande.
Bandi, S. et al., The mechanism of color generation in poly(ethylene terephthalate) / polyamide blends, Polymer Degradation and Stability, 2005, 88: pp. 341-348.
Böhme, H. et al., Untersuchungen in der Phthalimidin-Reihe, Die Pharmazie, 1970, 25: pp. 283-289.
Buhleier, E., et al., 2,6-Bis(aminomethyl)pyridine als Komplexligand und neues Kronenethersynthon, Justus Liebigs Annalen der Chemie, 1978, No. 4: pp. 537-544.
Chen et al., Efficient enhancement of DNA cleavage activity by introducing guanidinium groups into diiron(III) complex, Bioorganic & Medicinal Chemistry Letters, Pergamon, Elsevier Science, GB, vol. 18, No. 1, Nov. 5, 2007 (Nov. 5, 2007), pp. 109-113.
Database PubChem Compound [Online], NCBI; (Sep. 7, 2005), XP002724996, Database accession No. CID 3317391.

(56) References Cited

OTHER PUBLICATIONS

Grawe, T. et al., Self-Assembly of Ball-Shaped Molecular Complexes in Water, Journal of Organic Chemistry, 2002, vol. 67(11): pp. 3755-3763.
Hu, Y.S. et al., Improving Transparancy of stretched PET/MXD6 blends by modifying PET with isophthalate, Polymer, Elsevier Science, vol. 46 No. 14 Jun. 2005 pp. 5202-5210.
Keenan, R.M. et al., Conformational Preferences in a Benzodiazepine Series of Potent Nonpeptide Fibrinogen Receptor Antagonists, Journal of Medicinal Chemistry, 1999, vol. 42(4): pp. 545-559.
Kricheldorf, H.R., 15N NMR Spectroscopy 28-Solvent Effects on the 15N—13C Coupling Constants of Amides, Imides, Ureas and Polypeptides, OMR Organic Magnetic Resonance, 1980, vol. 14(6): pp. 455-561.
M Knollmüller, 1,2,4,5-Tetrahydro-3,2,4-benzothiadiazepin-3,3-dioxide und 1,2,3,5,6,7-Hexahydro-4,3,5-benzothiadiazonin-4,4-dioxide, Monatshefte für Chemie, 1974, 105, pp. 114-122.
Mauro Vieira de Almeida et al., Thalidomide Analogs from Diamines: Synthesis and Evaluation as Inhibitors of TNF-[alpha] Production, Chemical & Pharmaceutical Bulletin, 2007, vol. 55(2): pp. 223-226.
Ragusa, A. et al, Novel Enantioselective Receptors for N-Protected; Glutamate and Aspartate, Chemistry—A European Journal, vol. 11, No. 19, Sep. 19, 2005 (Sep. 19, 2005), pp. 5674-5688.
Rosevear, J., et al., A Comparison of the Reactions of Some Ethyl N-Arylcarbamates with Those of the Corresponding Acetanilides. II Amidomethylation with N-Hydroxymethylphthalimide, Austr. J. Chem., 1990, vol. 43(2): pp. 339-353.
Rossi, S. et al., A Highly Enantioselective Receptor for N-Protected Glutamate and Anomalous Solvent-Dependent Binding Properties, Angew. Chem. Int. Ed., vol. 41, No. 22, 2002, pp. 4233-4236.
Shigeyoshi Hara et al., Allylic Polymers, 1: Synthesis of Polyallyl Compounds Containing 4-Oxycarbonylphthalimido Units and Their Polymers, Die Makromolekulare Chemie, 1975, vol. 176(1): pp. 127-141.
Vacca, A. et al., A New Tripodal Receptor for Molecular Recognition of Monosaccharides. A Paradigm for Assessing Glycoside Binding Affinities and Selectivities by 1H NMR Spectroscopy, Journal of the American Chemical Society, 2004, vol. 126(50): pp. 16456-16465.
Yoshito, T. et al., Novel Self-Assembly of m-Xylylene Type Dithioureas by Head-to-Tail Hydrogen Bonding, J. org. Chem., 1998, vol. 63: pp. 7481-7489.
Zhanthin et al., The synthesis of fluorine-containing azamacrocyclic; compounds, Heterocycles, International Journal for Reviews and Communications in Heterocyclic Chemistry, (1992) 34(9):1729-1736.
Examination Report dated Sep. 20, 2012 for AU Pat. App. No. 2008251476, national phase of Intl. App. No. PCT/US2008/063250, filed May 9, 2008 (Inventor—G. Deshpande et al.; Applicant—Constar International, Inc.; pp. 1-3).
Notice of Allowance was dated Jan. 20, 2016 by the Canadian Patent Office for Canadian Application No. 2687081 which was filed on May 9, 2008 (Inventor—Girish N. Deshpande) (1 page).
Response to Office Action was dated Oct. 1, 2015 to the Canadian Patent Office for Canadian Application No. 2687081, which was filed on May 9, 2008 (Inventor—Girish N. Deshpande) (4 pages).
First Office Action was dated Apr. 1, 2015 by the Canadian Patent Office for Canadian Application No. 2687081, which was filed on May 9, 2008 (Inventor—Girish N. Deshpande) (3 pages).
Response to Office Action filed on Mar. 27, 2012 for CL Pat. App. No. 1391/2008, national phase of Intl. App. No. PCT/US2008/063250, filed May 9, 2008 (Inventor—G. Deshpande et al.; Applicant—Constar International, Inc.; pp. 1-21).
Office Action dated Sep. 30, 2011 for CL Pat. App. No. 1391-08, national phase of Intl. App. No. PCT/US2008/063250, filed May 9, 2008 (Inventor—G. Deshpande et al.; Applicant—Constar International, Inc.; pp. 1-21).

Third Office Action was dated Jan. 5, 2013 for CN Pat. App. No. 200880023116.X, national phase of Intl. App. No. PCT/US2008/063250, filed May 9, 2008 (Inventor—G. Deshpande et al.; Applicant—Constar International, Inc.; pp. 1-11).
Second Office Action was dated Mar. 16, 2012 for CN Pat. App. No. 200880023116.X, national phase of Intl. App. No. PCT/US2008/063250, filed May 9, 2008 (Inventor—G. Deshpande et al.; Applicant—Constar International, Inc.; pp. 1-11).
Response to Office Action filed on Dec. 21, 2011 for CN Pat. App. No. 200880023116.X, which is national phase of Intl. App. No. PCT/US2008/063250, filed May 9, 2008 (Inventor—G. Deshpande et al.; Applicant—Constar International, Inc.; pp. 1-37).
First Office Action dated Jul. 6, 2011 for CN Pat. App. No. 200880023116.X, which is national phase of Intl. App. No. PCT/US2008/063250, filed May 9, 2008 (Inventor—G. Deshpande et al.; Applicant—Constar International, Inc.; pp. 1-7).
First Office Action dated Dec. 11, 2015 for Chinese Application No. 2013106426272, which was filed on Dec. 3, 2013 and published as CN104017241 on Sep. 3, 2014 (Inventor—G. Deshpande et al.; Applicant—Constar International, Inc.; Original—3 pages// Translated—6 pages).
Preliminary Amendment filed on Dec. 10, 2009 for EP Pat. App. No. 08795847.6, which is national phase of Intl. App. No. PCT/US2008/063250, filed May 9, 2008 (Inventor—G. Deshpande et al.; Applicant—Constar International, Inc.; pp. 1-5).
Communication pursuant to Article 94(3) EPC dated Mar. 18, 2016 for EP Pat. App. No. 14150235.1, filed Jan. 6, 2014 (Inventor—G. Deshpande et al.; Applicant—Constar International, Inc.; pp. 1-2).
Response to Communication pursuant to Article 94(3) EPC dated Dec. 7, 2015 for EP Pat. App. No. 14150235.1, filed Jan. 6, 2014 (Inventor—G. Deshpande et al.; Applicant—Constar International, Inc.; pp. 1-2).
Communication pursuant to Article 94(3) EPC dated May 28, 2015 for EP Pat. App. No. 14150235.1, filed Jan. 6, 2014 (Inventor—G. Deshpande et al.; Applicant—Constar International, Inc.; pp. 1-4).
Extended European Search Report dated Jun. 17, 2014 for EP Pat. App. No. 14150235.1, filed Jan. 6, 2014 (Inventor—G. Deshpande et al.; Applicant—Constar International, Inc.; pp. 1-9).
Response to First Examination Report was dated Dec. 10, 2015 for Indian Application No. 7423/DELNP/2009, which was filed on May 9, 2008 (Inventor—G. Deshpande et al.) (pp. 1-262).
First Examination Report was dated Dec. 19, 2014 for Indian Application No. 7423/DELNP/2009, which was filed on May 9, 2008 (Inventor—G. Deshpande et al.) (pp. 1-2).
First Office Action was dated Jun. 30, 2016 by the Japanese Patent Office for Japanese Application No. 2015-249201, which was filed on Dec. 22, 2015 (Inventor—Girish N. Deshpande et al) (Original 2 pages// Translated 2 pages).
Response to Office Action filed on Aug. 20, 2012 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-2).
Office Action dated Apr. 19, 2012 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-2).
Response to Office Action filed on Feb. 3, 2012 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-4).
Office Action dated Sep. 23, 2011 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-3).
International Preliminary Report on Patentability dated Nov. 10, 2009 for Intl. App. No. PCT/US2008/063250, filed May 9, 2008 (Inventor—G. Deshpande et al.; Applicant—Constar International, Inc.; pp. 1-7).
International Search Report with Written Opinion dated Oct. 29, 2008 for Intl. App. No. PCT/US2008/063250, filed May 9, 2008 (Inventor—G. Deshpande et al.; Applicant—Constar International, Inc.; pp. 1-14).

(56) References Cited

OTHER PUBLICATIONS

Office Action was dated Mar. 30, 2015 by the Taiwan Patent Office for Taiwan Application No. 103123705 which was filed on Jul. 19, 2014 and published as 201439163 on Oct. 16, 2014 (Inventor—Girish N. Deshpande) (10 pages).
Notice of Allowance was dated Jan. 5, 2016 by the Taiwan Patent Office for Taiwan Application No. 103123705 which was filed on Jul. 19, 2014 and published as 201439163 on Oct. 16, 2014 (Inventor—Girish N. Deshpande) (3 pages).
Notice of Allowance dated Jun. 24, 2011 for U.S. Appl. No. 12/117,849, filed May 9, 2008 (Inventor—G. Deshpande et al.; Applicant—Constar International, Inc.; pp. 1-7).
Response after Non-Final Office Action filed on Apr. 8, 2011 for U.S. Appl. No. 12/117,849, filed May 9, 2008 (Inventor—G. Deshpande et al.; Applicant—Constar International, Inc.; pp. 1-16).
Non-Final Office Action dated Jan. 20, 2011 for U.S. Appl. No. 12/117,849, filed May 9, 2008 (Inventor—G. Deshpande et al.; Applicant—Constar International, Inc.; pp. 1-5).
Response to Election/Restriction Requirement filed on Dec. 17, 2010 for U.S. Appl. No. 12/117,849, filed May 9, 2008 (Inventor—G. Deshpande et al.; Applicant—Constar International, Inc.; pp. 1-3).
Requirement for Restriction/Election dated Oct. 5, 2010 for U.S. Appl. No. 12/117,849, filed May 9, 2008 (Inventor—G. Deshpande et al.; Applicant—Constar International, Inc.; pp. 1-5).
Notice of Allowance dated Dec. 23, 2011 for U.S. Appl. No. 13/164,477, filed Jun. 20, 2011 (Inventor—G. Deshpande et al.; Applicant—Constar International, Inc.; pp. 1-8).
Notice of Appeal was dated Dec. 19, 2014 to the U.S. Patent and Trademark Office for U.S. Appl. No. 13/849,797, filed Mar. 25, 2013 and published as US-2014-0027339-A1 on Jan. 30, 2014 (Inventor—Girish N. Deshpande) (2 pages).
Notice of Allowance was dated Jun. 8, 2016 to the U.S. Patent and Trademark Office for U.S. Appl. No. 13/849,797, filed Mar. 25, 2013 and published as US-2014-0027339-A1 on Jan. 30, 2014 (Inventor—Girish N. Deshpande) (7 pages).
Response to ExParte Quayle Action was mailed on May 5, 2016 to the U.S. Patent and Trademark Office for U.S. Appl. No. 13/849,797, filed Mar. 25, 2013 and published as US-2014-0027339-A1 on Jan. 30, 2014 (Inventor—Girish N. Deshpande) (2 pages).
ExParte Quayle Action was issued on Nov. 5, 2015 by the U.S. Patent and Trademark Office for U.S. Appl. No. 13/849,797, filed Mar. 25, 2013 and published as US-2014-0027339-A1 on Jan. 30, 2014 (Inventor—Girish N. Deshpande) (5 pages).
Final Office Action dated Jun. 19, 2014 for U.S. Appl. No. 13/849,797, filed Mar. 25, 2013 (Inventor—G. Deshpande et al.; Applicant—Constar International, Inc.; pp. 1-4).
Response after Non-Final Office Action filed on Jun. 4, 2014 for U.S. Appl. No. 13/849,797, filed Mar. 25, 2013 (Inventor—G. Deshpande et al.; Applicant—Constar International, Inc.; pp. 1-17).
Non-Final Office Action dated Dec. 5, 2013 for U.S. Appl. No. 13/849,797, filed Mar. 25, 2013 (Inventor—G. Deshpande et al.; Applicant—Constar International, Inc.; pp. 1-6).
Preliminary Amendment filed on Oct. 15, 2013 for U.S. Appl. No. 13/849,797, filed Mar. 25, 2013 (Inventor—G. Deshpande et al.; Applicant—Constar International, Inc.; pp. 1-14).
Preliminary Amendment filed on Mar. 25, 2013 for U.S. Appl. No. 13/849,797, filed Mar. 25, 2013 (Inventor—G. Deshpande et al.; Applicant—Constar International, Inc.; pp. 1-3).
Preliminary Amendment filed on Nov. 21, 2012 for EP Pat. App. No. 10822439.5, national phase of Intl. App. No. PCT/US2010/050719, dated Sep. 29, 2010 (Inventor—G. Deshpande; Applicant—Constar International, Inc.; pp. 1-15).
International Preliminary Report on Patentability dated Apr. 12, 2012 for Intl. App. No. PCT/US2010/050719, dated Sep. 29, 2010 (Inventor—G. Deshpande; Applicant—Constar International, Inc.; pp. 1-5).

International Search Report with Written Opinion dated Jun. 27, 2011 for Intl. App. No. PCT/US2010/050719, dated Sep. 29, 2010 (Inventor—G. Deshpande; Applicant—Constar International, Inc.; pp. 1-7).
Examination Report was dated Sep. 10, 2015 by the Australian Patent Office for Australian Application No. 2010303748, which was filed on Sep. 29, 2010 (Inventor—Girish N. Deshpande) (2 pages).
Office Action was dated Apr. 21, 2016 by the Canadian Patent Office for Canadian Application No. 2779714, which was filed on Sep. 29, 2010 (Inventor—Girish N. Deshpande) (3 pages).
Supplementary European Search Report was dated Jul. 30, 2013 by the European Patent Office for Application No. 10822439.5, which was filed on Sep. 29, 2010 and published as 2483342 on Aug. 8, 2012 (Inventor—Girish N. Deshpande) (6 pages).
Amendment/Request for Re-consideration after Non Final Rejection was dated Jul. 11, 2016 to the U.S. Patent and Trademark Office for U.S. Appl. No. 12/893,817, filed Sep. 29, 2010 and published as US 2011-0123741 A1 on May 26, 2011 (Inventor—Girish N. Deshpande) (39 pages).
Non Final Rejection was dated Jan. 11, 2016 by the U.S. Patent and Trademark Office for U.S. Appl. No. 12/893,817, filed Sep. 29, 2010 and published as US 2011-0123741 A1 on May 26, 2011 (Inventor—Girish N. Deshpande) (11 pages).
Amendment/Request for Re-consideration after Non Final Rejection was dated Sep. 4, 2015 to the U.S. Patent and Trademark Office for U.S. Appl. No. 12/893,817, filed Sep. 29, 2010 and published as US 2011-0123741 A1 on May 26, 2011 (Inventor—Girish N. Deshpande) (19 pages).
Non-Final Office Action dated Mar. 4, 2015 for U.S. Appl. No. 12/893,817, filed Sep. 29, 2010 and published as US 2011-0123741 A1 on May 26, 2011(Inventor—G. Deshpande; Applicant Constar International, Inc.; pp. 1-9).
Examiner Initiated Interview Summary dated Dec. 12, 2014 for U.S. Appl. No. 12/893,817, filed Sep. 29, 2010 (Inventor—G. Deshpande; Applicant—Constar International, Inc.; pp. 1-3).
Response to Final Office Action with Request for Continued Examination filed on Dec. 1, 2014 for U.S. Appl. No. 12/893,817, filed Sep. 29, 2010 (Inventor—G. Deshpande; Applicant—Constar International, Inc.; pp. 1-20).
Advisory Action dated May 19, 2014 for U.S. Appl. No. 12/893,817, filed Sep. 29, 2010 (Inventor—G. Deshpande; Applicant—Constar International, Inc.; pp. 1-9).
Amendment and Response to Final Office Action after Notice of Appeal filed on May 1, 2014 for U.S. Appl. No. 12/893,817, filed Sep. 29, 2010 and published as US 2011-0123741 A1 on May 26, 2011 (Inventor—G. Deshpande; Applicant—Constar International, Inc.; pp. 1-20).
Notice of Appeal filed on May 1, 2014 for U.S. Appl. No. 12/893,817, filed Sep. 29, 2010 (Inventor—G. Deshpande; Applicant—Constar International, Inc.; pp. 1-1).
Final Office Action dated Nov. 1, 2013 for U.S. Appl. No. 12/893,817, filed Sep. 29, 2010 (Inventor—G. Deshpande; Applicant—Constar International, Inc.; pp. 1-10).
Response to Non-Final Office Action filed on Aug. 14, 2013 for U.S. Appl. No. 12/893,817, filed Sep. 29, 2010 and published as US 2011-0123741 A1 on May 26, 2011 (Inventor—G. Deshpande; Applicant—Constar International, Inc.; pp. 1-19).
Non Final Office Action dated Feb. 14, 2013 for U.S. Appl. No. 12/893,817, filed Sep. 29, 2010 and published as US 2011-0123741 A1 on May 26, 2011 (Inventor—G. Deshpande et al.; Applicant—Constar International, Inc.; pp. 1-8).
Response to Election/Restriction Requirement filed on Aug. 10, 2012 for U.S. Appl. No. 12/893,817, filed Sep. 29, 2010 and published as US 2011-0123741 A1 on May 26, 2011 (Inventor—G. Deshpande et al.; Applicant—Constar International, Inc.; pp. 1-2).
Requirement for Restriction/Election dated May 9, 2012 for U.S. Appl. No. 12/893,817, filed Sep. 29, 2010 and published as US 2011-0123741 A1 on May 26, 2011 (Inventor—G. Deshpande et al.; Applicant—Constar International, Inc.; pp. 1-8).

(56) References Cited

OTHER PUBLICATIONS

International Preliminary Report on Patentability dated May 24, 2012 for Intl. App. No. PCT/US2010/056594, dated Nov. 12, 2010 (Inventor—G. Deshpande; Applicant—Constar International, Inc.; pp. 1-5).
International Search Report with Written Opinion dated Jul. 28, 2011 for Intl. App. No. PCT/US2010/056594, dated Nov. 12, 2010 (Inventor—G. Deshpande; Applicant—Constar International, Inc.; pp. 1-8).
Notice of Allowance dated Jun. 30, 2015 for U.S. Appl. No. 12/945,351, filed Nov. 12, 2010 (Inventor—G. Deshpande; Applicant—Constar International, Inc.; pp. 1-7).
Response after Non-Final Office Action filed on May 18, 2015 for U.S. Appl. No. 12/945,351, filed Nov. 12, 2010 (Inventor—G. Deshpande; Applicant—Constar International, Inc.; pp. 1-7).
Non-Final Office Action dated Nov. 18, 2014 for U.S. Appl. No. 12/945,351, filed Nov. 12, 2010 (Inventor—G. Deshpande; Applicant—Constar International, Inc.; pp. 1-6).
Examiner Initiated Interview Summary dated Nov. 18, 2014 for U.S. Appl. No. 12/945,351, filed Nov. 12, 2010 (Inventor—G. Deshpande; Applicant—Constar International, Inc.; pp. 1-1).
Response after Final Office Action filed on Oct. 7, 2014 for U.S. Appl. No. 12/945,351, filed Nov. 12, 2010 (Inventor—G. Deshpande; Applicant—Constar International, Inc.; pp. 1-7).
Final Office Action dated May 7, 2014 for U.S. Appl. No. 12/945,351, filed Nov. 12, 2010 (Inventor—G. Deshpande; Applicant—Constar International, Inc.; pp. 1-6).
Response after Non-Final Office Action filed on Mar. 4, 2014 for U.S. Appl. No. 12/945,351, filed Nov. 12, 2010 (Inventor—G. Deshpande; Applicant—Constar International, Inc.; pp. 1-34).
Non-Final Office Action dated Sep. 3, 2013 for U.S. Appl. No. 12/945,351, filed Nov. 12, 2010 (Inventor—G. Deshpande; Applicant—Constar International, Inc.; pp. 1-6).
Response to Requirement for Restriction/Election filed on Jun. 20, 2013 for U.S. Appl. No. 12/945,351, filed Nov. 12, 2010 (Inventor—G. Deshpande; Applicant—Constar International, Inc.; pp. 1-3).
Requirement for Restriction/Election dated Dec. 20, 2012 for U.S. Appl. No. 12/945,351, filed Nov. 12, 2010 (Inventor—G. Deshpande; Applicant—Constar International, Inc.; pp. 1-8).
Response to Requirement for Restriction/Election filed on Oct. 12, 2012 for U.S. Appl. No. 12/945,351, filed Nov. 12, 2010 (Inventor—G. Deshpande et al.; Applicant—Constar International, Inc.; pp. 1-3).
Requirement for Restriction/Election dated Jun. 12, 2012 for U.S. Appl. No. 12/945,351, filed Nov. 12, 2010 (Inventor—G. Deshpande et al.; Applicant—Constar International, Inc.; pp. 1-10).
International Preliminary Report on Patentability dated May 24, 2012 for Intl. App. No. PCT/US2010/056598, dated Nov. 12, 2010 (Inventor—G. Deshpande; Applicant—Constar International, Inc.; pp. 1-7).
International Search Report with Written Opinion dated Aug. 2, 2011 for Intl. App. No. PCT/US2010/056598, dated Nov. 12, 2010 (Inventor—G. Deshpande; Applicant—Constar International, Inc.; pp. 1-13).
Supplementary European Search Report was dated Aug. 27, 2015 by the European Patent Office for Application No. 10830821.4, which was filed on Nov. 12, 2010 and published as 2499182 on Sep. 19, 2012 (Inventor—Girish N. Deshpande) (2 pages).
European Search Opinion was dated Aug. 27, 2015 by the European Patent Office for Application No. 10830821.4, which was filed on Nov. 12, 2010 and published as 2499182 on Sep. 19, 2012 (Inventor—Girish N. Deshpande) ) (5 pages).
Notice of Allowance dated Jan. 22, 2014 for U.S. Appl. No. 12/945,353, filed Nov. 12, 2010 (Inventor—G. Deshpande; Applicant—Constar International, Inc.; pp. 1-5).
Response after Non-Final Office Action filed on Oct. 29, 2013 for U.S. Appl. No. 12/945,353, filed Nov. 12, 2010 (Inventor—G. Deshpande; Applicant—Constar International, Inc.; pp. 1-10).
Non-Final Office Action dated Apr. 29, 2013 for U.S. Appl. No. 12/945,353, filed Nov. 12, 2010 (Inventor—G. Deshpande; Applicant—Constar International, Inc.; pp. 1-8).
Response to Election/Restriction Requirement filed on Mar. 4, 2013 for U.S. Appl. No. 12/945,353, filed Nov. 12, 2010 (Inventor—G. Deshpande; Applicant—Constar International, Inc.; pp. 1-3).
Requirement for Restriction/Election dated Nov. 2, 2012 for U.S. Appl. No. 12/945,353, filed Nov. 12, 2010 (Inventor—G. Deshpande et al.; Applicant—Constar International, Inc.; pp. 1-10).
Notice of Allowance dated Oct. 2, 2014 for U.S. Appl. No. 12/258,823, filed Apr. 22, 2014 (Inventor—G. Deshpande; Applicant—Constar International, Inc.; pp. 1-14).
Preliminary Amendment was dated Oct. 15, 2015 to the U.S. Patent and Trademark Office for U.S. Appl. No. 14/585,413, filed Dec. 30, 2014 (Inventor—Girish N. Deshpande) (pp. 1-9).
Response to Communication pursuant to Article 94(3) EPC dated Apr. 5, 2016 for EP Pat. App. No. 10830816.4, filed Nov. 12, 2010 and published as 2499134 on Sep. 19, 2012 (Inventor—G. Deshpande et al.; pp. 1-2).
Communication pursuant to Article 94(3) EPC dated Jun. 19, 2015 for EP Pat. App. No. 10830816.4, filed Nov. 12, 2010 and published as 2499134 on Sep. 19, 2012 (Inventor—G. Deshpande et al.; pp. 1-2).
Response to Communication pursuant to Article 94(3) EPC dated Oct. 24, 2014 for EP Pat. App. No. 10830816.4, filed Nov. 12, 2010 and published as 2499134 on Sep. 19, 2012 (Inventor—G. Deshpande et al.; pp. 1-2).
Communication pursuant to Article 94(3) EPC dated Apr. 14, 2014 for EP Pat. App. No. 10830816.4, filed Nov. 12, 2010 and published as 2499134 on Sep. 19, 2012 (Inventor—G. Deshpande et al.; pp. 1-2).
Extended European Search Report dated Mar. 9, 2013 for EP Pat. App. No. 10830816.4, and published as 2499134 on Sep. 19, 2012 (Inventor—G. Deshpande; Applicant—Constar International, Inc.; pp. 1-7).
International Preliminary Report on Patentability dated May 24, 2012 for Intl. App. No. PCT/US2010/056585, dated Nov. 12, 2010 (Inventor—G. Deshpande; Applicant—Constar International, Inc.; pp. 1-6).
International Search Report with Written Opinion dated Jul. 25, 2011 for Intl. App. No. PCT/US2010/056585, dated Nov. 12, 2010 (Inventor—G. Deshpande; Applicant—Constar International, Inc.; pp. 1-8).
Examination Report was dated Sep. 4, 2015 by the Australian Patent Office for Australian Application No. 2010319384, which was filed on Nov. 12, 2010 (Inventor—Girish N. Deshpande) (4 pages).
Notice of Allowance dated Jan. 16, 2013 for U.S. Appl. No. 12/945,355, filed Nov. 12, 2010 (Inventor—G. Deshpande et al.; Applicant—Constar International, LLC; pp. 1-5).
Notice of Allowance dated Sep. 26, 2012 for U.S. Appl. No. 12/945,355, filed Nov. 12, 2010 (Inventor—G. Deshpande et al.; Applicant—Constar International, LLC; pp. 1-19).
Response to Election/Restriction Requirement filed on Aug. 7, 2012 for U.S. Appl. No. 12/945,355, filed Nov. 12, 2010 (Inventor—G. Deshpande et al.; Applicant—Constar International, LLC; pp. 1-6).
Requirement for Restriction/Election dated May 7, 2012 for U.S. Appl. No. 12/945,355, filed Nov. 12, 2010 (Inventor—G. Deshpande et al.; Applicant—Constar International, LLC; pp. 1-11).
Preliminary Amendment was dated Jul. 11, 2016 to the U.S. Patent and Trademark Office for U.S. Appl. No. 14/976,766, filed Dec. 21, 2015 (Inventor—Girish N. Deshpande) (pp. 1-5).
Second Office Action dated Sep. 19, 2016 for Chinese Application No. 2013106426272, which was filed on Dec. 3, 2013 and published as CN104017241 on Sep. 3, 2014 (Inventor—G. Deshpande et al.; Applicant—Constar International, Inc.; Original—4 pages// Translated—7 pages).
Issue Notification was dated Oct. 5, 2016 to the U.S. Patent and Trademark Office for U.S. Appl. No. 13/849,797, filed Mar. 25, 2013 and published as US-2014-0027339-A1 on Jan. 30, 2014 (Inventor—Girish N. Deshpande) (1 pages).
Communication under Rule 71(3) EPC dated Sep. 7, 2016 for EP Pat. App. No. 10822439.5, filed Sep. 29, 2010 (Inventor—G. Deshpande et al.; Applicant—Constar International, Inc.; pp. 1-67).

(56) References Cited

OTHER PUBLICATIONS

Final Rejection was dated Aug. 29, 2016 to the U.S. Patent and Trademark Office for U.S. Appl. No. 12/893,817, filed Sep. 29, 2010 and published as US 2011-0123741 A1 on May 26, 2011 (Inventor—Girish N. Deshpande) (5 pages).
Issue Notification dated Oct. 21, 2015 for U.S. Appl. No. 12/945,351, filed Nov. 12, 2010 (Inventor—G. Deshpande; Applicant—Constar International, Inc.; pp. 1-7).
Office Action was dated Sep. 13, 2016 by the Canadian Patent Office for Canadian Application No. 2,780,746, which was filed on Nov. 12, 2010 (Inventor—Girish N. Deshpande) (4 pages).
Issue Notification dated Feb. 18, 2015 for U.S. Appl. No. 12/258,823, filed Apr. 22, 2014 (Inventor—G. Deshpande; Applicant—Constar International, Inc.; 1 page).
Notice of Allowance dated Feb. 10, 2015 for U.S. Appl. No. 12/258,823, filed Apr. 22, 2014 (Inventor—G. Deshpande; Applicant—Constar International, Inc.; pp. 1-2).
Non Final Rejection was dated Sep. 30, 2016 to the U.S. Patent and Trademark Office for U.S. Appl. No. 14/585,413, filed Dec. 30, 2014 (Inventor—Girish N. Deshpande) (pp. 1-8).
Office Action was dated Jul. 27, 2016 by the Canadian Patent Office for Canadian Application No. 2,780,768, which was filed on Nov. 12, 2010 (Inventor—Girish N. Deshpande) (4 pages).
Issue Notification dated May 8, 2013 for U.S. Appl. No. 12/945,355, filed Nov. 12, 2010 (Inventor—G. Deshpande et al.; Applicant—Constar International, LLC; 1 page).
Requirement for Restriction/Election dated Apr. 24, 2014 for U.S. Appl. No. 13/889,133, filed May 7, 2013 (Inventor—G. Deshpande et al.; Applicant—Constar International, Inc.; pp. 1-9).
Response to Requirement for Restriction/Election was dated 49/24/2014 to the U.S. Appl. No. 13/889,133, filed May 7, 2013 (Inventor—G. Deshpande et al.; Applicant—Constar International, Inc.; pp. 1-4).
Non Final Rejection dated Jan. 15, 2015 for U.S. Appl. No. 13/889,133, filed May 7, 2013 (Inventor—G. Deshpande et al.; Applicant—Constar International, Inc.; pp. 1-6).
Response to Non Final Rejection was dated Jul. 14, 2015 to the U.S. Appl. No. 13/889,133, filed May 7, 2013 (Inventor—G. Deshpande et al.; Applicant—Constar International, Inc.; pp. 1-10).
Notice of Allowance was dated Aug. 17, 2015 for U.S. Appl. No. 13/889,133, filed May 7, 2013 (Inventor—G. Deshpande et al.; Applicant—Constar International, Inc.; pp. 1-8).
Issue Notification was dated Dec. 9, 2015 for U.S. Appl. No. 13/889,133, filed May 7, 2013 (Inventor—G. Deshpande et al.; Applicant—Constar International, Inc.; pp. 1-8).
Second Office Action was dated Mar. 31, 2017 by the Canadian Intellectual Property Office for CA Application No. 2780768, which was filed on Nov. 12, 2010 and published as CA 2780768 A1 on May 19, 2011 (Applicant—Plastipak Packaging, Inc.) (3 pages).
Office Action was dated Apr. 13, 2017 by the Russian Patent Office for RU Application No. 2013142425, which was filed on Sep. 17, 2013 and published as RU 2013142425 A on Apr. 10, 2015 (Applicant—Plastipak Packaging, Inc.) (Original—5 pages// Translated—3 pages).
Office Action was dated May 23, 2017 by the Canadian Intellectual Property Office for CA Application No. 2780746, which was filed on Nov. 12, 2010 and published as CA 2780746 A1 on May 19, 2011 (Applicant—Plastipak Packaging, Inc.) (3 pages).
Final Rejection was dated Jun. 13, 2017 by the USPTO for U.S. Appl. No. 14/585,413, filed Dec. 30, 2014 and published as US 2016-0376404 A1 on Dec. 29, 2016 (Applicant—Plastipak Packaging, Inc.) (3 pages).
Australian Examination Report was dated Dec. 1, 2016 by the Australian Patent Office for AU Application No. 2016203377, which was filed on May 4, 2016 and published as (Applicant—Plastipak Packaging, Inc.) (3 pages).
Decision of Refusal was dated Jan. 23, 2017 by SIPO for JP Application No. 2015-249201, which was filed on Dec. 22, 2015 (Applicant—Plastipak Packaging, Inc.) (Original 2 pages// Translated 2 pages).

Office Action was dated Jan. 16, 2017 by the Canadian Patent Office for CA Application No. 2,779,714, which was filed on Sep. 29, 2010 (Applicant—Plastipak Packaging, Inc.) (3 pages).
Communication pursuant to Article 94(3) EPC was dated Dec. 16, 2016 by the European Patent Office for EP Application No. 10830821.4, which was filed on Nov. 12, 2010 and published as 2499182 on Sep. 19, 2012 (Applicant—Plastipak Packaging, Inc.) (6 pages).
Restriction Requirement was dated Dec. 29, 2016 by the U.S. Patent and Trademark Office for U.S. Appl. No. 14/976,766, filed Dec. 21, 2015 and published as US 2016-0311771 A1 on Oct. 27, 2016 (Applicant—Plastipak Packaging, Inc.) (7 pages).
Office Action and Search Report was dated Jan. 11, 2017 by the Russian Patent Office for RU Application No. 2014148149, which was filed on Apr. 30, 2013 and published as 17 on Jun. 20, 2016 (Applicant—Plastipak Packaging, Inc.) (8 pages).
Office Action was dated Feb. 14, 2017 by Japanese Patent Office for JP Application No. 2015-510375, which was filed on Apr. 30, 2013 (Applicant—Plastipak Packaging, Inc.) (Original—5 // Translated—7 pages).
Office Action was dated Feb. 13, 2017 by the Canadian Patent Office for CA Application No. 2,893,166, which was filed on Feb. 15, 2016 (Applicant—Plastipak Packaging, Inc.) (3 pages).
Non Final Rejection was dated Feb. 27, 2017 by the U.S. Patent and Trademark Office for U.S. Appl. No. 14/466,717, filed Aug. 22, 2014 and published as US 2016-0052694 A1 on Feb. 25, 2016 (Applicant—Plastipak Packaging, Inc.) (35 pages).
Non Final Rejection was dated Jan. 27, 2017 by the U.S. Patent and Trademark Office for U.S. Appl. No. 14/517,643, filed Aug. 22, 2014 and published as US 2016-0108207 A1 on Apr. 21, 2016 (Applicant—Plastipak Packaging, Inc.) (12 pages).
Second Office Action was dated Jan. 3, 2017 by SIPO for CN Application No. 201380025753.1, which was filed on Apr. 30, 2013 and published as 104379654 on Feb. 25, 2015 (Applicant—Plastipak Packaging Inc.) (Original—5 pages // Translation—8 pages).
Second Office Action dated Jul. 11, 2017 by the Argentinian Patent Office for Patent Application No. P080102003, which was filed on May 12, 2008 (Inventor—Deshpande et al.; Applicant—Plastipak Packaging, Inc.) (Original—5 pages // Translation—3 pages).
Notice of Acceptance dated Nov. 30, 2017 by the Intellectual Property Office of Australia for Patent Application No. 2016203377, which was filed on May 4, 2016 (Inventor—Deshpande et al.; Applicant—Plastipak Packaging, Inc.) (3 pages).
Certificate of Patent dated Dec. 13, 2017 by the European Patent Office for Patent Application No. 14150235.1, which was filed on Jan. 6, 2014 and issued as 2754690 on Dec. 13, 2017 (Inventor—Deshpande et al.; Applicant—Plastipak Packaging, Inc.) (1 page).
Office Action dated Nov. 3, 2017 by the Intellectual Property Office of Mexico for Patent Application No. MX/a/2013/001496, which was filed on Feb. 6, 2013 (Inventor—Deshpande et al.; Applicant—Plastipak Packaging, Inc.) (Original—4 pages; Translation—2 pages).
Decision to Grant dated Nov. 15, 2017 by the Patent Office of the Russian Federation for Patent Application No. 2013142425, which was filed on Sep. 17, 2013 (Inventor—Deshpande et al.; Applicant—Plastipak Packaging, Inc.) (Original—22 pages; Translation—20 pages).
Non-Final Office Action dated Sep. 27, 2017 by the U.S. Patent and Trademark Office for U.S. Appl. No. 15/147,532, filed May 5, 2016 and published as US 2017/0088332 on Mar. 30, 2017 (Inventor—Deshpande et al.; Applicant—Plastipak Packaging, Inc.) (6 pages).
Office Action dated Aug. 30, 2017 by the Canadian Intellectual Property Office for Patent Application No. 2779714, which was filed on Sep. 29, 2010 and published on Apr. 14, 2011 (Inventor—Deshpande; Applicant—Plastipak Packaging, Inc.) (3 pages).
Response to Non-Final Office Action filed on Aug. 7, 2017 with the U.S. Patent and Trademark Office for U.S. Appl. No. 12/893,817, filed Sep. 29, 2010 and published as US 2011/0123741 on May 26, 2011 (Inventor—Deshpande; Applicant—Plastipak Packaging, Inc.) (17 pages).
Notice of Allowance dated Sep. 15, 2017 by the U.S. Patent and Trademark Office for U.S. Appl. No. 12/893,817, filed Sep. 29, 2010

(56) References Cited

OTHER PUBLICATIONS and published as US 2011/0123741 on May 26, 2011 (Inventor—Deshpande; Applicant—Plastipak Packaging, Inc.) (10 pages).
Issue Notification dated Jan. 31, 2018 by the U.S. Patent and Trademark Office for U.S. Appl. No. 12/893,817, filed Sep. 29, 2010 and published as US 2011/0123741 on May 26, 2011 (Inventor—Deshpande; Applicant—Plastipak Packaging, Inc.) (1 page).
Examination Report No. 1 dated Mar. 24, 2017 by the Intellectual Property Office of Australia for Patent Application No. 2016200734, which was filed on Feb. 5, 2016 and published on Mar. 3, 2016 (Inventor—Deshpande; Applicant—Plastipak Packaging, Inc.) (4 pages).
Office Action dated Jul. 25, 2017 by the Canadian Intellectual Property Office for Patent Application No. 2780749, which was filed on Nov. 12, 2010 and published on May 19, 2011 (Inventor—Deshpande; Applicant—Plastipak Packaging, Inc.) (3 pages).
Supplementary European Search Report and Opinion dated Dec. 13, 2017 by the European Patent Office for Patent Application No. 10830818.0, which was filed on Dec. 12, 2010 and published as EP2499195 on Sep. 19, 2012 (Inventor—Deshpande; Applicant—Plastipak Packaging, Inc.) (6 pages).
Examination Report No. 1 dated Mar. 24, 2017 by the Intellectual Property Office of Australia for Patent Application No. 2016200891, which was filed on Feb. 11, 2016 and published on Mar. 3, 2016 (Inventor—Deshpande; Applicant—Plastipak Packaging, Inc.) (3 pages).
Notice of Appeal Filed filed on Dec. 13, 2017 by the U.S. Patent and Trademark Office for U.S. Appl. No. 14/585,413, filed Dec. 30, 2014 and published as US 2016/0376404 on Dec. 29, 2016 (Inventor—Deshpande et al.; Applicant—Plastipak Packaging, Inc.) (2 pages).
Office Action dated Nov. 27, 2017 by the Canadian Intellectual Property Office for Patent Application No. 2,780,768, which was filed on Nov. 12, 2010 2016 (Inventor—Deshpande; Applicant—Plastipak Packaging, Inc.) (3 pages).
Intention to Grant dated Nov. 2, 2017 by the European Patent Office for Patent Application No. 10830816.4, which was filed on Nov. 12, 2010 and published as EP2499134 on Sep. 19, 2012(Inventor—Deshpande; Applicant—Plastipak Packaging, Inc.) (6 pages).
Ex Parte Quayle Action issued on Sep. 22, 2017 by the U.S. Patent and Trademark Office for U.S. Appl. No. 14/976,766, filed Dec. 21, 2015 and published as US 2016/0311771 on Oct. 27, 2016 (Inventor—Deshpande; Applicant—Plastipak Packaging, Inc.) (7 pages).

\* cited by examiner

OXYGEN SCAVENGERS, COMPOSITIONS COMPRISING THE SCAVENGERS, AND ARTICLES MADE FROM THE COMPOSITIONS

CROSS-REFERENCE TO RELATED APPLICATIONS

This application is a continuation of co-pending U.S. application Ser. No. 12/945,351 filed Nov. 12, 2010, which claims the benefit of and priority to U.S. Provisional Patent Application No. 61/261,158, filed Nov. 13, 2009, which are incorporated herein by reference in their entireties.

BACKGROUND

It is known in the art to include an oxygen scavenger in the packaging structure for the protection of oxygen sensitive materials. Such scavengers are believed to react with oxygen that is trapped in the package or that permeates from outside of the package, thus extending to life of package contents. These packages include films, bottles, containers, and the like. Food, beverages (such as beer and fruit juices), cosmetics, medicines, and the like are particularly sensitive to oxygen exposure and require high barrier properties to oxygen to preserve the freshness of the package contents and avoid changes in flavor, texture and color.

Use of certain polyamides in combination with a transition metal is known to be useful as the oxygen scavenging material. One particularly useful polyamide is MXD6 which contains meta-xylene residues in the polymer chain. See, for example, U.S. Pat. Nos. 5,639,815; 5,049,624; and 5,021,515.

Other oxygen scavengers include potassium sulfite (U.S. Pat. No. 4,536,409), unsaturated hydrocarbons (U.S. Pat. No. 5,211,875), and ascorbic acid derivatives (U.S. Pat. No. 5,075,362).

In barrier layers of packaging walls that are made from blends of oxygen scavenging materials with base polymer resins such as PET, haze can result due to such factors as the immiscibility of the scavenging materials with the base polymer resins and the inability to create by mechanical blending means disperse-phase domains that are so small as not to interfere with the passage of light therethrough; and the adverse influence of the scavenging material on the crystallization behavior of PET base resin. One approach to minimizing such haze is careful selection of base resin to improve dispersibility of the scavenger material and, thus, reduce, but not substantially eliminate, haze; and to minimize the adverse crystallization effect. This approach may undesirably narrowly restrict the choice of base polymer resin. Another approach is to use compositions that serve as compatibilizers to reduce haze. These approaches add cost to the layer and the compatibilizer adds an additional material that must be evaluated for its suitability for contact with food. Thus, there is a need in the art for improved materials which provide high oxygen scavenging capability and are substantially transparent.

SUMMARY

The melt blended polymer compositions disclosed herein comprise:
a) a thermoplastic polymer; and
b) a transition metal in a positive oxidation state, the metal present in an amount of from about 10 ppm to about 400 ppm c) a compound having the formula:

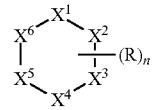

wherein $X^1$, $X^2$, $X^3$, $X^4$, $X^5$, and $X^6$ are each independently:
  i) $=CR^1-$;
  ii) $=N-$;
  iii) $-O-$; or
  iv) $-S-$;
  or when an R group is present, $R^1$ is equal to R;
each $R^1$ is independently chosen from:
  i) hydrogen;
  ii) $C_1$-$C_{12}$ substituted or unsubstituted linear, branched, or cyclic alkyl;
  iii) $C_2$-$C_{12}$ substituted or unsubstituted linear, branched, or cyclic alkenyl;
  iv) $C_2$-$C_{12}$ substituted or unsubstituted linear or branched alkynyl;
  v) $C_6$ or $C_{10}$ substituted or unsubstituted aryl;
  vi) $C_1$-$C_9$ substituted or unsubstituted heterocyclic;
  vii) $C_1$-$C_{11}$ substituted or unsubstituted heteroaryl;
  viii) halogen;
  ix) $-[C(R^{23a})(R^{23b})]_xOR^{10}$;
    $R^{10}$ is chosen from:
    a) $-H$;
    b) $C_1$-$C_{12}$ substituted or unsubstituted linear, branched, or cyclic alkyl;
    c) $C_6$ or $C_{10}$ substituted or unsubstituted aryl or alkylenearyl;
    d) $C_1$-$C_9$ substituted or unsubstituted heterocyclic;
    e) $C_1$-$C_{11}$ substituted or unsubstituted heteroaryl;
  x) $-[C(R^{23a})(R^{23b})]_xN(R^{11a})(R^{11b})$;
    $R^{11a}$ and $R^{11b}$ are each independently chosen from:
    a) $-H$;
    b) $-OR^{12}$;
      $R^{12}$ is hydrogen or $C_1$-C4 linear alkyl;
    c) $C_1$-$C_{12}$ substituted or unsubstituted linear, branched, or cyclic alkyl;
    d) $C_6$ or $C_{10}$ substituted or unsubstituted aryl;
    e) $C_1$-$C_9$ substituted or unsubstituted heterocyclic;
    f) $C_1$-$C_{11}$ substituted or unsubstituted heteroaryl; or
    g) $R^{11a}$ and $R^{11b}$ can be taken together to form a substituted or unsubstituted ring having from 3 to 10 carbon atoms and from 0 to 3 heteroatoms chosen from oxygen, nitrogen, and sulfur;
  xi) $-[C(R^{23a})(R^{23b})]_xC(O)R^{13}$;
    $R^{13}$ is:
    a) $C_1$-$C_{12}$ substituted or unsubstituted linear, branched, or cyclic alkyl;
    b) $-OR^{14}$;
      $R^{14}$ is hydrogen, substituted or unsubstituted $C_1$-$C_4$ linear alkyl, $C_6$ or $C_{10}$ substituted or unsubstituted aryl, $C_1$-$C_9$ substituted or unsubstituted heterocyclic, $C_1$-$C_{11}$ substituted or unsubstituted heteroaryl;
    c) $-N(R^{15a})(R^{15b})$;
      $R^{15a}$ and $R^{15b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;

xii) $-[C(R^{23a})(R^{23b})]_xOC(O)R^{16}$;

$R^{16}$ is:
a) $C_1$-$C_{12}$ substituted or unsubstituted linear, branched, or cyclic alkyl;
b) $-N(R^{17a})(R^{17b})$;
  $R^{17a}$ and $R^{17b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{17a}$ and $R^{17b}$ can be taken together to form a substituted or unsubstituted ring having from 3 to 10 carbon atoms and from 0 to 3 heteroatoms chosen from oxygen, nitrogen, and sulfur;

xiii) $-[C(R^{23a})(R^{23b})]_xNR^{18}C(O)R^{19}$;

$R^{18}$ is:
a) $-H$; or
b) $C_1$-$C_4$ substituted or unsubstituted linear, branched, or cyclic alkyl;

$R^{19}$ is:
a) $C_1$-$C_{12}$ substituted or unsubstituted linear, branched, or cyclic alkyl;
b) $-N(R^{20a})(R^{20b})$;
  $R^{20a}$ and $R^{20b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{20a}$ and $R^{20b}$ can be taken together to form a substituted or unsubstituted ring having from 3 to 10 carbon atoms and from 0 to 3 heteroatoms chosen from oxygen, nitrogen, and sulfur;

xiv) $-[C(R^{23a})(R^{23b})]_xCN$;
xv) $-[C(R^{23a})(R^{23b})]_xNO_2$;
xvi) $-[C(R^{23a})(R^{23b})]_xR^{21}$;

$R^{21}$ is $C_1$-$C_{10}$ linear, branched, or cyclic alkyl substituted by from 1 to 21 halogen atoms chosen from $-F$, $-Cl$, $-Br$, or $-I$;

xvii) $-[C(R^{23a})(R^{23b})]_xSO_2R^{22}$;

$R^{22}$ is hydrogen, hydroxyl, substituted or unsubstituted $C_1$-$C_4$ linear or branched alkyl; substituted or unsubstituted $C_6$, $C_{10}$, or $C_{14}$ aryl; $C_7$-$C_{15}$ alkylenearyl; $C_1$-$C_9$ substituted or unsubstituted heterocyclic; or $C_1$-$C_{11}$ substituted or unsubstituted heteroaryl; or xviii) $R^1$ units on two adjacent carbons can be taken together to form a substituted or unsubstituted 5, 6, or 7 member fused ring comprising one or more heteroatoms chosen from nitrogen, oxygen, or sulfur, and wherein the fused ring can be substituted by $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or when one of the ring atoms is a carbon, the atom can be substituted with carbonyl having the formula $=O$, or imide having the formula $=NH$;

$R^{23a}$ and $R^{23b}$ are each independently hydrogen or $C_1$-$C_4$ alkyl; and the index x is an integer from 0 to 5;

R is has the formula:

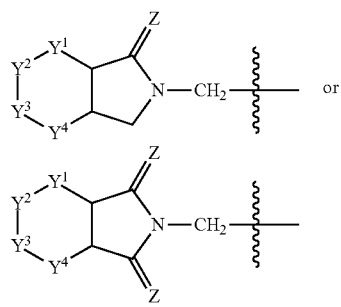

each Z is independently O, NH, or S;
$Y^1$, $Y^2$, $Y^3$, and $Y^4$ are each independently:
  i) $=CR^2-$; or
  ii) $=N-$;
each $R^2$ is independently chosen from:
i) hydrogen;
ii) substituted or unsubstituted $C_1$-$C_{10}$ linear, branched, or cyclic alkyl;
iii) substituted or unsubstituted $C_2$-$C_{10}$ linear, branched, or cyclic alkenyl;
iv) substituted or unsubstituted $C_2$-$C_{10}$ linear or branched alkynyl;
v) substituted or unsubstituted $C_6$ or $C_{10}$ aryl;
vi) substituted or unsubstituted $C_1$-$C_9$ heterocyclic;
vii) substituted or unsubstituted $C_1$-$C_9$ heteroaryl; or
  two $R^2$ units on adjacent carbon atoms can be taken together to form a substituted or unsubstituted heterocyclic or substituted or unsubstituted heteroaryl ring having from form 2 to 20 carbon atoms and from 1 to 7 heteroatoms; and n is an integer from 0 to 6

Also disclosed herein are methods of making the disclosed compositions.

Also disclosed herein are methods of preparing articles from the disclosed compositions.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Figure 1:
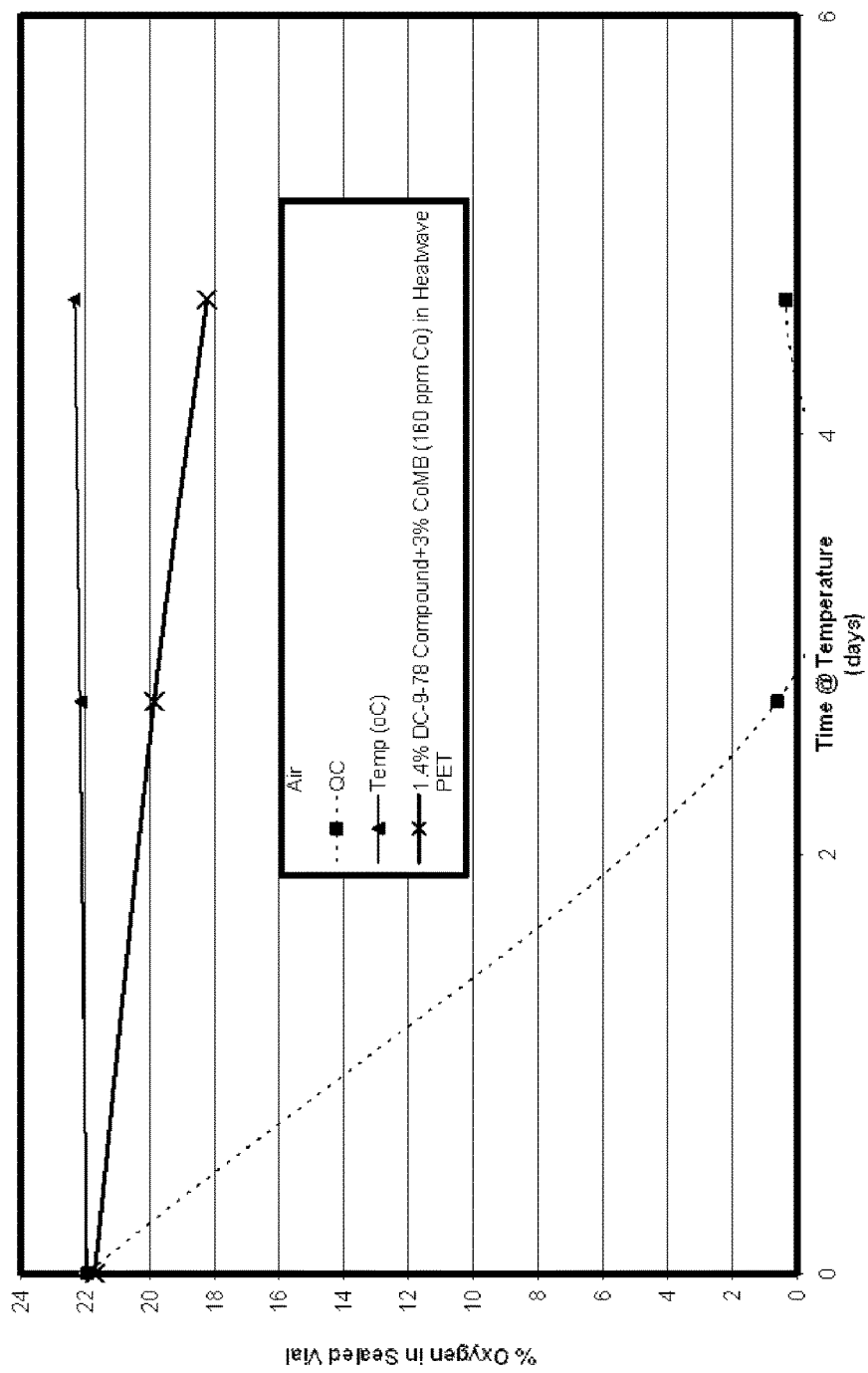
FIG. 1 is a plot showing oxygen scavenging ability of a disclosed composition.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a carrier" includes mixtures of two or more such carriers, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

As used herein, "master batch" refers to a mixture of base polymer, oxidizable organic component, and transition metal that will be diluted, typically with at least additional base polymer, prior to forming an article. As such, the concentrations of oxidizable organic component and transition metal are higher than in the formed article.

"Admixture" or "blend" is generally used herein means a physical combination of two or more different components.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed, for example, in Advanced Organic Chemistry by J. March, 1985, pp. 16-18.

As used herein, the description of one or more method steps does not preclude the presence of additional method steps before or after the combined recited steps. Additional steps can also be intervening steps to those described. In addition, it is understood that the lettering of process steps or ingredients is a convenient means for identifying discrete activities or ingredients and the recited lettering can be arranged in any sequence.

Where a range of numbers is presented in the application, it is understood that the range includes all integers and fractions thereof between the stated range limits. A range of numbers expressly includes numbers less than the stated endpoints and those in-between the stated range. A range of from 1-3, for example, includes the integers one, two, and three as well as any fractions that reside between these integers.

The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units can comprise only carbon atoms in the ring (carbocyclic and aryl rings) or can comprise one or more heteroatoms in the ring (heterocyclic and heteroaryl). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and Unsubstituted Acyclic Hydrocarbyl:

For the purposes of the present disclosure the term "substituted and unsubstituted acyclic hydrocarbyl" encompasses 3 categories of units:

1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.

2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and Unsubstituted Cyclic Hydrocarbyl:

For the purposes of the present disclosure the term "substituted and unsubstituted cyclic hydrocarbyl" encompasses 5 categories of units:

1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:

i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).
  ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decalinyl ($C_{10}$), decahydroazulenyl ($C_{10}$).
  iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:
  i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).
  ii) $C_6$ or $C_{10}$ aryl rings fused with 1 or 2 saturated rings non-limiting examples of which include, bicyclo[4.2.0]octa-1,3,5-trienyl ($C_8$), and indanyl ($C_9$).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which comprises the heteroatom is also not an aromatic ring." The following are non-limiting examples of "substituted and unsubstituted heterocyclic rings" which encompass the following categories of units:
  i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), thiazolidinyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$).
  ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:
  i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), isoxazolyl ($C_3$), isothiazolyl ($C_3$), furanyl ($C_4$), thiopheneyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$).
  ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

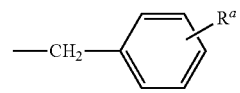

wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl $C_1$-($C_6$), 2-(3-hydroxy-phenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkylene-heteroaryl units, for example a 2-picolyl $C_1$-($C_6$) unit having the formula:

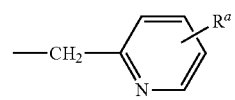

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

For the purposes of the present disclosure carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present disclosure, and to provide consistency in defining the present disclosure, fused ring units, as well as spirocyclic rings, bicyclic rings and the like, which comprise a single heteroatom will be characterized and referred to herein as being encompassed by the cyclic family corresponding to the heteroatom containing ring, although the artisan can have alternative characterizations. For example, 1,2,3,4-tetrahydroquinoline having the formula:

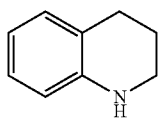

is, for the purposes of the present disclosure, considered a heterocyclic unit. 6,7-Dihydro-5H-cyclopentapyrimidine having the formula:

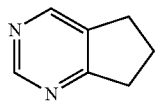

is, for the purposes of the present disclosure, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the disclosure. For example, 1,2,3,4-tetrahydro-[1,8]naphthyridine having the formula:

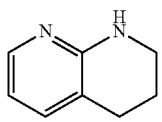

is, for the purposes of the present disclosure, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms can be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

Polymer Composition

Disclosed herein are polymer compositions comprising one or more oxygen scavengers. The oxygen scavengers can be added during the formation of the polymer composition or the oxygen scavengers can be formed in situ during the formulation of the composition, during the formation of an article of manufacture comprising the composition, or upon curing or other process step chosen by the formulator. The end product oxygen scavenger can be formed in situ by the degradation of a precursor or, alternatively, the oxygen scavenger can result from the break down of an oxygen scavenger in the course of the first scavenger successfully scavenging oxygen.

As such, disclosed herein are polymer compositions comprising:
a) a thermoplastic polymer; and
b) a compound having the formula:

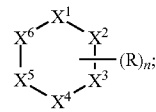

wherein the index n represents the number of R units attached to the core ring. The value of n is an integer from 0 to 6. Each $X^1$, $X^2$, $X^3$, $X^4$, $X^5$, and $X^6$ is independently chosen from:
i) =CR$^1$—;
ii) =N—;
iii) —O—; or
iv) —S—;
or when one or more R groups are present on the ring, i.e., n is not equal to 0, then the $X^1$, $X^2$, $X^3$, $X^4$, $X^5$, or $X^6$ to which the R unit is attached will have the corresponding formula =CR—.

For example, a compound having the formula:

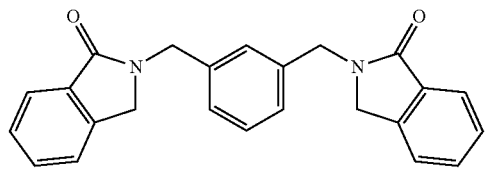 [SMILES: O=C1c2ccccc2CN1Cc1cccc(CN2Cc3ccccc3C2=O)c1]

is represented by the formula:

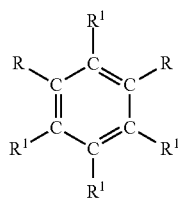

wherein $X^1$, $X^3$, $X^4$, and $X^5$ are =CR$^1$—; $X^6$ and $X^2$ are =CR—; and the index n is equal to 2.

As further defined herein, two adjacent $R^1$ units can be taken together to form a fused ring system, for example, a ring system having the formula:

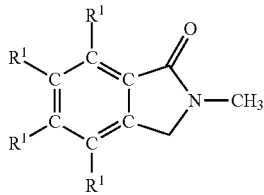

wherein $R^1$ can be hydrogen or any substitute for hydrogen as defined herein.

The following are non-limiting examples of units which can substitute for hydrogen when $R^1$ is not a hydrogen atom:

i) $C_1$-$C_{12}$ substituted or unsubstituted linear, branched, or cyclic alkyl; for example, methyl ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), iso-propyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), pentyl ($C_5$), cyclopentyl ($C_5$), hexyl ($C_6$), and cyclohexyl ($C_6$), and the like;

ii) $C_2$-$C_{12}$ substituted or unsubstituted linear, branched, or cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), cyclobutenyl ($C_4$), cyclopentenyl ($C_5$), cyclopentadienyl ($C_5$), cyclohexenyl ($C_6$), 7-hydroxy-7-methyloct-4-en-2-yl ($C_9$), and 7-hydroxy-7-methyloct-3,5-dien-2-yl ($C_9$), and the like;

iii) $C_2$-$C_{12}$ substituted or unsubstituted linear or branched alkynyl; for example, ethynyl ($C_2$), prop-2-ynyl (also propargyl) ($C_3$), propyn-1-yl ($C_3$), 2-methyl-hex-4-yn-1-yl ($C_7$); 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like;

iv) $C_6$ or $C_{10}$ substituted or unsubstituted aryl; for example, phenyl, 2-chlorophenyl, 3-hydroxyphenyl, 4-nitrophenyl, 2-fluoro-4-methylphenyl, 3,5-dinitrophenyl, 8-hydroxynaphth-1-yl, 6-sulfonylnapth-2-yl, and the like;

v) $C_1$-$C_9$ substituted or unsubstituted heterocyclic; for example, as defined further herein;

vi) $C_1$-$C_{11}$ substituted or unsubstituted heteroaryl; for example, as defined further herein;

vii) halogen; for example, fluoro, chloro, bromo, and iodo;
—$[C(R^{23a})(R^{23b})]_xOR^{10}$;
$R^{10}$ is chosen from:
  a) —H;
  b) $C_1$-$C_{12}$ substituted or unsubstituted linear, branched, or cyclic alkyl;
  c) $C_6$ or $C_{10}$ substituted or unsubstituted aryl or alkylenearyl;
  d) $C_1$-$C_9$ substituted or unsubstituted heterocyclic;
  e) $C_1$-$C_{11}$ substituted or unsubstituted heteroaryl;

ix) —$[C(R^{23a})(R^{23b})]_xN(R^{11a})(R^{11b})$;
$R^{11a}$ and $R^{11b}$ are each independently chosen from:
  a) —H;
  b) —$OR^{12}$;
    $R^{12}$ is hydrogen or $C_1$-C4 linear alkyl;
  c) $C_1$-$C_{12}$ substituted or unsubstituted linear, branched, or cyclic alkyl;
  d) $C_6$ or $C_{10}$ substituted or unsubstituted aryl;
  e) $C_7$-$C_{22}$ substituted or unsubstituted alkylenearyl;
  f) $C_1$-$C_9$ substituted or unsubstituted heterocyclic;
  g) $C_2$-$C_{20}$ substituted or unsubstituted alkyleneheterocyclic;
  h) $C_1$-$C_{11}$ substituted or unsubstituted heteroaryl;
  i) $C_2$-$C_{20}$ substituted or unsubstituted alkyleneheteroaryl; or
  j) $R^{11a}$ and $R^{11b}$ can be taken together to form a substituted or unsubstituted ring having from 3 to 10 carbon atoms and from 0 to 3 heteroatoms chosen from oxygen, nitrogen, and sulfur;

x) —$[C(R^{23a})(R^{23b})]_xC(O)R^{13}$;
$R^{13}$ is:
  a) $C_1$-$C_{12}$ substituted or unsubstituted linear, branched, or cyclic alkyl;
  b) —$OR^{14}$;
    $R^{14}$ is hydrogen, substituted or unsubstituted $C_1$-$C_4$ linear alkyl, $C_6$ or $C_{10}$ substituted or unsubstituted aryl, $C_1$-$C_9$ substituted or unsubstituted heterocyclic, $C_1$-$C_{11}$ substituted or unsubstituted heteroaryl;
  c) —$N(R^{15a})(R^{15b})$;
    $R^{15a}$ and $R^{15b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;

xi) —$[C(R^{23a})(R^{23b})]_xOC(O)R^{16}$;
$R^{16}$ is:
  a) $C_1$-$C_{12}$ substituted or unsubstituted linear, branched, or cyclic alkyl;
  b) —$N(R^{17a})(R^{17b})$;
    $R^{17a}$ and $R^{17b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{17a}$ and $R^{17b}$ can be taken together to form a substituted or unsubstituted ring having from 3 to 10 carbon atoms and from 0 to 3 heteroatoms chosen from oxygen, nitrogen, and sulfur;

xii) —$[C(R^{23a})(R^{23b})]_xNR^{18}C(O)R^{19}$;
$R^{18}$ is:
  a) —H; or
  b) $C_1$-$C_4$ substituted or unsubstituted linear, branched, or cyclic alkyl;
$R^{19}$ is:
  a) $C_1$-$C_{12}$ substituted or unsubstituted linear, branched, or cyclic alkyl;
  b) —$N(R^{20a})(R^{20b})$;
    $R^{20a}$ and $R^{20b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{20a}$ and $R^{20b}$ can be taken together to form a substituted or unsubstituted ring having from 3 to 10 carbon atoms and from 0 to 3 heteroatoms chosen from oxygen, nitrogen, and sulfur;

c) $R^{18}$ and $R^{19}$ can be taken together to form a heterocyclic ring, or a fused ring system having from 5 to 20 atoms and from 1 to 4 heteroatoms chosen from oxygen, nitrogen and sulfur;

xiii) —[C($R^{23a}$)($R^{23b}$)]$_x$CN;
xiv) —[C($R^{23a}$)($R^{23b}$)]$_x$NO$_2$;
xv) —[C($R^{23a}$)($R^{23b}$)]$_x$R$^{21}$;

$R^{21}$ is $C_1$-$C_{10}$ linear, branched, or cyclic alkyl substituted by from 1 to 21 halogen atoms chosen from —F, —Cl, —Br, or —I;

xvi) —[C($R^{23a}$)($R^{23b}$)]$_x$SO$_2$R$^{22}$;

$R^{22}$ is hydrogen, hydroxyl, substituted or unsubstituted $C_1$-$C_4$ linear or branched alkyl; substituted or unsubstituted $C_6$, $C_{10}$, or $C_{14}$ aryl; $C_7$-$C_{15}$ alkylenearyl; $C_1$-$C_9$ substituted or unsubstituted heterocyclic; or $C_1$-$C_{11}$ substituted or unsubstituted heteroaryl;

$R^{23a}$ and $R^{23b}$ are each independently hydrogen or $C_1$-$C_4$ alkyl; and the index x is an integer from 0 to 5.

R units have the formula:

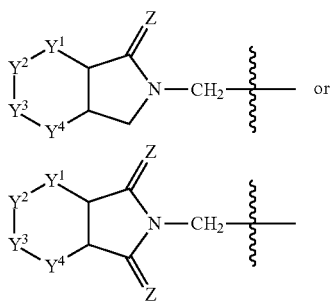

or wherein Z is O, NH, or S;
each $Y^1$, $Y^2$, $Y^3$, and $Y^4$ unit is independently chosen from:
  i) =CR$^2$—; or
  ii) =N—.
each $R^2$ unit is independently chosen from:
  i) hydrogen;
  ii) substituted or unsubstituted $C_1$-$C_{10}$ linear, branched, or cyclic alkyl;
  iii) substituted or unsubstituted $C_2$-$C_{10}$ linear, branched, or cyclic alkenyl;
  iv) substituted or unsubstituted $C_2$-$C_{10}$ linear or branched alkynyl;
  v) substituted or unsubstituted $C_6$ or $C_{10}$ aryl;
  vi) substituted or unsubstituted $C_1$-$C_9$ heterocyclic;
  vii) substituted or unsubstituted $C_1$-$C_9$ heteroaryl; or
    two $R^2$ units on adjacent carbon atoms can be taken together to form a substituted or unsubstituted heterocyclic or substituted or unsubstituted heteroaryl ring having from form 2 to 20 carbon atoms and from 1 to 7 heteroatoms.

In one aspect the disclosed compounds having one or more heteroatoms in the core ring, the compounds having the formula:

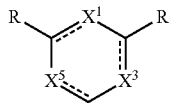

wherein $X^1$, $X^3$, and $X^5$ are each independently chosen from:
  i) =CR$^1$—;
  ii) =N—;
  iii) —O—; or
  iv) —S—,
and when $X^1$, $X^3$, or $X^5$ are equal to =CR$^1$— or =N— the dotted line - - - represents a potential bond and when $X^1$, $X^3$, or $X^5$ are equal to —O— or —S—, the potential bond represented by the dotted line is absent.

R units of this aspect have the formula:

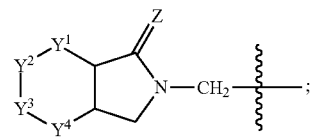

wherein each Z is independently O, NH, or S; and $Y^1$, $Y^2$, $Y^3$, and $Y^4$ are each independently:
  i) =CR$^2$—; or
  ii) =N—.

One iteration of this aspect relates to compounds wherein each $R^1$ is chosen from:
  i) —H;
  ii) —CH$_3$; or
  iii) —CHO.

Each $R^2$ is independently chosen from:
  i) hydrogen;
  ii) substituted or unsubstituted $C_1$-$C_{10}$ linear, branched, or cyclic alkyl;
  iii) substituted or unsubstituted $C_2$-$C_{10}$ linear, branched, or cyclic alkenyl;
  iv) substituted or unsubstituted $C_2$-$C_{10}$ linear or branched alkynyl;
  v) substituted or unsubstituted $C_6$ or $C_{10}$ aryl;
  vi) substituted or unsubstituted $C_1$-$C_9$ heterocyclic;
  vii) substituted or unsubstituted $C_1$-$C_9$ heteroaryl; or
  viii) two $R^2$ units on adjacent carbon atoms can be taken together to form a substituted or unsubstituted heterocyclic or substituted or unsubstituted heteroaryl ring having from form 2 to 20 carbon atoms and from 1 to 7 heteroatoms.

Non-limiting examples of this aspect include:

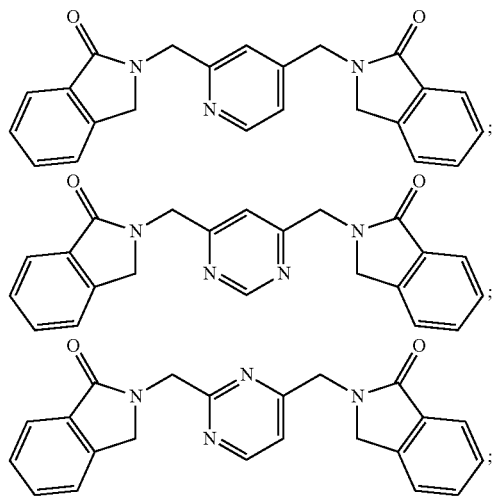

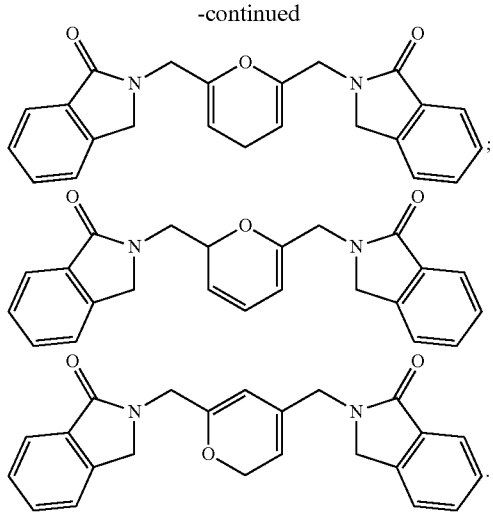

A further aspect relates to compound having the formula:

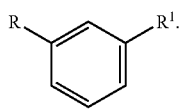

One embodiment of this aspect relates to compounds wherein R has the formula:

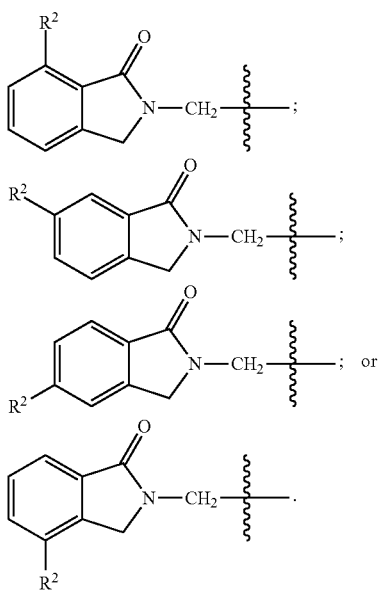

In one iteration of this embodiment, $R^2$ is chosen from groups having electron donating properties. Non-limiting examples of electron donating groups include hydroxy, lower alkoxy, lower alkyl, amino, lower alkylamino, di(lower alkyl)amino, aryloxy, mercapto, lower alkylthio, lower alkylmercapto, disulfide and the like, including combinations of these groups.

In another iteration of this embodiment, $R^2$ is chosen from groups having electron withdrawing properties. Non-limiting examples of electron withdrawing groups include fluoro, chloro, bromo, nitro, acyl, cyano, carboxyl, $C_2$-$C_8$ alkenyl, $C_2$-$C_8$ alkynyl, carboxaldehyde, carboxyamido, aryl, quaternary ammonium, trifluoro-methyl, alkoxycarbonyl, aryloxycarbonyl, aminocarbonyl, sulfonic, alkanesulfonyl, arylsulfonyl, perfluoroalkanesulfonyl, perfluoroarylsulfonyl, phosphoryl, tertiary amine cation and the like, including combinations of these groups.

In one embodiment, $R^1$ is $-[C(R^{23a})(R^{23b})]_xN(R^{11a})(R^{11b})$ as defined herein above. In one iteration, $R^{11a}$ is hydrogen, $R^{11b}$ is $C_7$-$C_{22}$ substituted or unsubstituted alkylenearyl, $R^{23a}$ and $R^{23b}$ are both hydrogen, and the index x is equal to 1, thereby providing $R^1$ units having the general formula $-CH_2NHR^{11b}$ wherein $R^{11b}$ is a suitable substituted benzyl, for example, compounds having the formula.

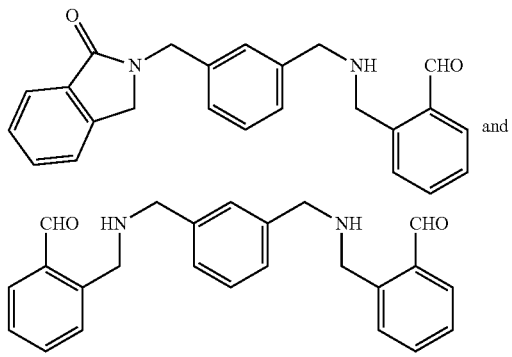

In another aspect, the compounds have the formula:

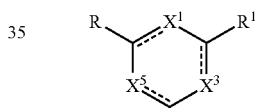

wherein $X^1$, $X^3$, and $X^5$ are each independently chosen from:
i) =$CR^1$—;
ii) =N—;
iii) —O—; or
iv) —S—,
and when $X^1$, $X^3$, or $X^5$ are equal to =$CR^1$— or =N— the dotted line - - - represents a bond and when $X^1$, $X^3$, or $X^5$ are equal to —O— or —S—, the bond represented by the dotted line is absent.

For this aspect, when $R^1$ is present, $R^1$ can be
i) —$CH_3$; or
ii) —CHO.
R has the formula:

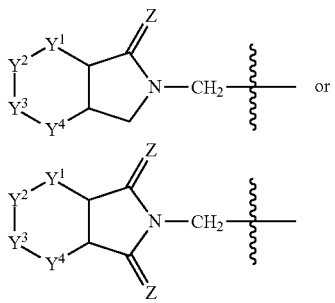

wherein each Z is independently O, NH, or S; and $Y^1$, $Y^2$, $Y^3$, and $Y^4$ are each independently:
  i) $=CR^2—$; or
  ii) $=N—$.
Each $R^2$ is independently chosen from:
  i) hydrogen;
  ii) substituted or unsubstituted $C_1$-$C_{10}$ linear, branched, or cyclic alkyl;
  iii) substituted or unsubstituted $C_2$-$C_{10}$ linear, branched, or cyclic alkenyl;
  iv) substituted or unsubstituted $C_2$-$C_{10}$ linear or branched alkynyl;
  v) substituted or unsubstituted $C_6$ or $C_{10}$ aryl;
  vi) substituted or unsubstituted $C_1$-$C_9$ heterocyclic;
  vii) substituted or unsubstituted $C_1$-$C_9$ heteroaryl; or
  viii) two $R^2$ units on adjacent carbon atoms can be taken together to form a substituted or unsubstituted heterocyclic or substituted or unsubstituted heteroaryl ring having from form 2 to 20 carbon atoms and from 1 to 7 heteroatoms.
$R^1$ is chosen from:
  i) $—CH_3$; or
  ii) $—CHO$.
One iteration of this aspect includes the following non-limiting examples:

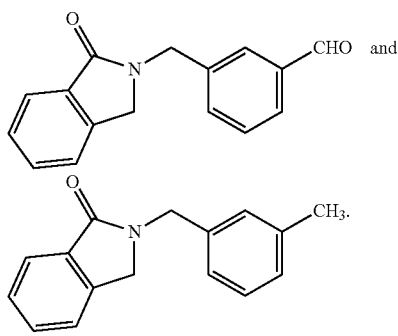

The oxygen scavengers described herein are present in an amount of about 1% to about 10% by weight based on the weight of the composition in some embodiments. In other embodiments, the oxygen scavenging compound is present in an amount of about 1% to about 5% by weight based on the weight of the composition. In still other embodiments, the compound is present in an amount of about 1% to about 3% by weight based on the weight of the composition. Also within the scope of the present disclosure are those embodiments were the oxygen scavengers described herein are present in an amount of about 0.1% to about 10% by weight based on the weight of the composition.

One embodiment disclosed herein further comprises from 30 to 150 ppm of one or more transition metals.

Other aspects of the disclosure relate to package walls comprising at least one layer, the layer comprising a composition, the composition comprising:
  a) a thermoplastic polymer;
  b) at least one compound of the disclosed oxygen scavengers; and
  c) at least one transition metal in a positive oxidation state, i.e., $M^{+m}$, wherein m is an integer from 1 to 8, the metal being present in the composition in an amount of from about 10 to about 400 ppm; wherein further the oxygen scavenger is present in an amount of about 0.10% to about 10% by weight of the composition.

Yet other aspects of the disclosure relate to package walls comprising a composition, the composition comprising:
  A) one or more outer layers; and
  B) one or more inner layers;
  wherein at least one of the inner or at least one of the outer layers comprises a composition comprising:
    a) a thermoplastic polymer;
    b) at least one compound of the disclosed oxygen scavengers; and
    c) at least one transition metal in a positive oxidation state, the metal being present in the composition in an amount of from about 10 to about 400 ppm; wherein further the oxygen scavenger is present in an amount of about 0.10% to about 10% by weight of the composition.

As it relates to this aspect, one embodiments relates to package walls wherein the first layer is disposed radially outward from the second layer.

Also disclosed herein are methods for packaging an oxygen sensitive material comprising:
  A) preparing a package having a wall comprising at least one layer, at least one of the layers comprising a composition, the composition comprising
    a) a thermoplastic polymer;
    b) at least one compound of the disclosed oxygen scavengers; and
    c) at least one transition metal in a positive oxidation state, the metal being present in the composition in an amount of from about 10 to about 400 ppm; wherein further the oxygen scavenger is present in an amount of about 0.10% to about 10% by weight of the composition;
  B) introducing the oxygen sensitive material into the package; and
  C) closing the package.

Still further disclosed herein are methods for producing a packaging material having a wall with oxygen barrier properties comprising:
  A) combining a thermoplastic polymer with at least one of the oxygen scavengers disclosed herein to form a composition, wherein the composition has at least one transition metal in a positive oxidation state, the metal being present in the composition in an amount of from about 10 to about 400 ppm; wherein further the oxygen scavenger is present in an amount of about 0.10% to about 10% by weight of the composition;
  B) forming the product of step (A) into a wall; and
  C) forming a container which comprises the wall.

Another aspect of the disclosure concerns processes for making an article comprising:
  A) forming a melt by combining in a melt processing zone:
    a) a thermoplastic polymer;
    b) at least one compound of the disclosed oxygen scavengers; and
    c) at least one transition metal in a positive oxidation state, the metal being present in the composition in an amount of from about 10 to about 400 ppm; wherein further the oxygen scavenger is present in an amount of about 0.10% to about 10% by weight of the composition; and
  B) forming an article from the melt.

In some embodiments, the article is a preform, a sheet, a bottle, a cup, or a jar.

The antioxidant/oxygen scavengers disclosed herein can be used in a broad range of organic products normally subject to gradual degradation in the presence of oxygen during use over an extended period. One embodiment disclosed herein relates to organic compositions protected by the present antioxidants that are of the type wherein the art recognizes the need for antioxidant protection and to which an antioxidant a known antioxidant is customarily added to obtain an extended service life. The oxidative degradation that this protects against is the slow gradual deterioration of the organic composition rather than, for example, combustion. In other words, the disclosed additives are not necessarily flame retarding additives nor flame suppressing.

In some embodiments, the antioxidant/oxygen scavenger can be utilized at elevated temperatures. One such use would be during a melt processing operation.

Antioxidants/Oxygen Scavengers

The disclosed oxygen scavengers can be prepared by the procedures outlined below in the various schemes and as described in the Examples herein.

One category of oxygen scavenger relates to compounds having the formula:

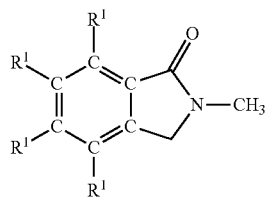

wherein $R^1$ can be hydrogen or any substitute for hydrogen as defined herein above. Scheme I and Example 1 provide a non-limiting example of the preparation of compounds according to this category.

Scheme I

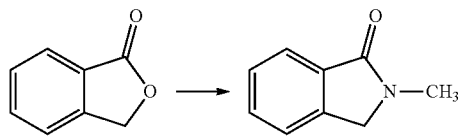

Reagents and conditions: CH$_3$NH$_2$ (aq.); xylene; reflux.

Example 1—Prophetic Preparation of Substituted and Unsubstituted 2-Methylisoindolin-1-one To a 500 mL 3-neck flask fitted with a Dean-Stark trap/condenser, magnetic stirring, and an addition funnel, isobenzofuran-1(3H)-one (13.4 g, 100 mmol) and xylene (250 mL) can be charged. With good stirring, a solution of methyl amine (100 mmol in xylene) can be slowly added. The course of the reaction can be followed by TLC. When the starting materials appear consumed, the flask can be heated and water collected until the theoretical amount is obtained. After a removal of the xylene under reduced pressure, the product can be obtained by crystallization or purification over silica.

Example 2—Preparation of n-metaxylylene-2,3-dihydro-1H-isoindol-1-one

Twenty-nine grams of phthalide (0.216 mol) and twenty five grams of 3-methylbenzyl amine (0.206 mol) are combined in a 1 L Parr reactor. The reactor is evacuated to 26" of vacuum. The vacuum is broken with nitrogen, and the reactor is pressurized to 10 psig with nitrogen, The reactor is heated to 165° C., and heat is maintained until the pressure of the reactor reaches 70 psig. The reactor is rapidly cooled. This yielded 51 grams of dark oil. The oil is placed in a sublimating vessel, and heated to 70° C. with <25 mmHg vacuum, for approximately 6 hours. Unreacted phthalide sublimes overhead, and is discarded. The remaining oil is dissolved in heptane, and extracted with 2% HCl water. The heptane layer is treated with carbon, and the carbon is removed by centrifugation. The heptane is removed from the product layer by heating to 30° C. under 25 mmHg vacuum. The results in a clear yellow oil, 25 grams ((~0.105 mol)) (51% yield). Boiling Point >200° C./25 mm Hg. This reaction is schematically depicted in Scheme 2 below:

Scheme II

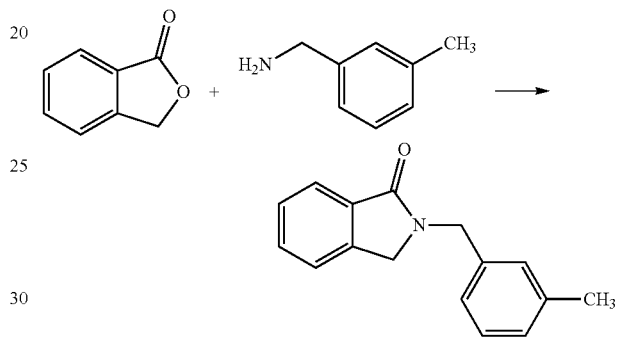

Reagents and conditions: xylene; reflux.

The resulting product from Example 2 was tested by HPLC and GC. Conditions for GC are as follows: 30 m DB-17, 0.32 mm i.d. The initial temperature was 50° C., for 3 minutes with a temperature ramp of 10° C./min, followed by a final temperature of 250° C. for 10 minutes. The methanol test solvent eluted at 1.0 minute. 3-methylbenzyl amine eluted at 3.3 minutes. Phthalide eluted at 15.5 minutes. The product eluted at 26.9 minutes.

HPLC conditions are as follows. HPLC was performed on a C18 column, 15 cm×4.6 mm i.d. 5 micron. Detection was at 254 nm. The mobile phase elution profile is tabulated below.

| Time | water | methanol | Flow |
| --- | --- | --- | --- |
| 0.00 | 90 | 10 | 1.500 ml/min |
| 8.00 | 20 | 80 | 1.500 ml/min |
| 13.00 | 20 | 80 | 1.500 ml/min |
| 17.00 | 90 | 10 | 1.500 ml/min |
| 19.00 | 90 | 10 | 1.500 ml/min |

Example 3—Hot Melt Preparation

The n-metaxylylene-2,3-dihydro-1H-isoindol-1-one (DC-9-78) was prepared according to Example 2 having up to 90% purity. This liquid compound was physically blended with hot, dry PET resin (Heatwave CF746 from Eastman Chemicals) and a PET based Cobalt Neodecanoate Masterbatch. The Heatwave CF746 PET resin was dried in Matsui dryer at 310° F. for ~6 hrs with air dew point of −40° F. The final compositions were melt-blended in a BOY 22 S injection molder as follows: PET=95.6% (w/w), compound n-metaxylylene-2,3-dihydro-1H-isoindol-1 one=1.4% (w/w) and PET based Cobalt Neodecanoate Masterbatch=3% (w/w) (160 ppm Co). The BOY 22 S injection molder barrel temperatures during injection molding was ~270° C. for both zones, the injection pressure was ~600 psi, nozzle heater and sprue heater temperatures were ~275° C. The mold was water cooled.

Plaques formed from the above composition were collected and tested for oxygen scavenging ability using Oxysense™. The plaques were ground to fine powder, placed in a sealed glass vial, with a photoluminescent window on the wall. The intensity of light reflected from the photoluminescent window is proportional to the oxygen content in the vial. The Oxysense™ data for the above composition and a control composition comprised of Constar International's DC-100 is shown in FIG. 1. As seen from the data of FIG. 1, the compound n-metaxylylene-2,3-dihydro-1H-isoindol-1 one does scavenge oxygen when melt-blended with cobalt catalyst in a PET matrix.

Example 4—Hot Melt Preparation

The compound 2-benzyl-1-isoindolinone (DCX-300-1) was prepared by reacting benzyl amine with phthalide (2-benzofuran-1(3H)-one. The chemical structure of 2-benzyl-1-isoindolinone is shown below:

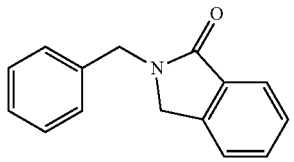 [SMILES: O=C1c2ccccc2CN1Cc1ccccc1]

1.4 weight % of this compound (lot number LP 081710, prepared by Cymer LLC, Decatur, Tenn.) was mixed with dried Eastlon CB-651S PET resin (lot number 0104896, manufactured by Far Eastern Textiles) and 80 ppm cobalt catalyst (added as a solid masterbatch of Cobalt Neodecanoate in PET). The PET resin was dried in a Piovan dryer at 170° C. for 4 hours before being used for mixing. The mixture was fed into the BOY 22 S injection molding machine to mold plaques. The BOY 22 S injection molder barrel temperatures during injection molding was ~275° C. for both heating zones, the injection pressure was ~700 psi, nozzle heater and sprue heater temperatures were ~280° C. The mold was water cooled.

Figure 2:
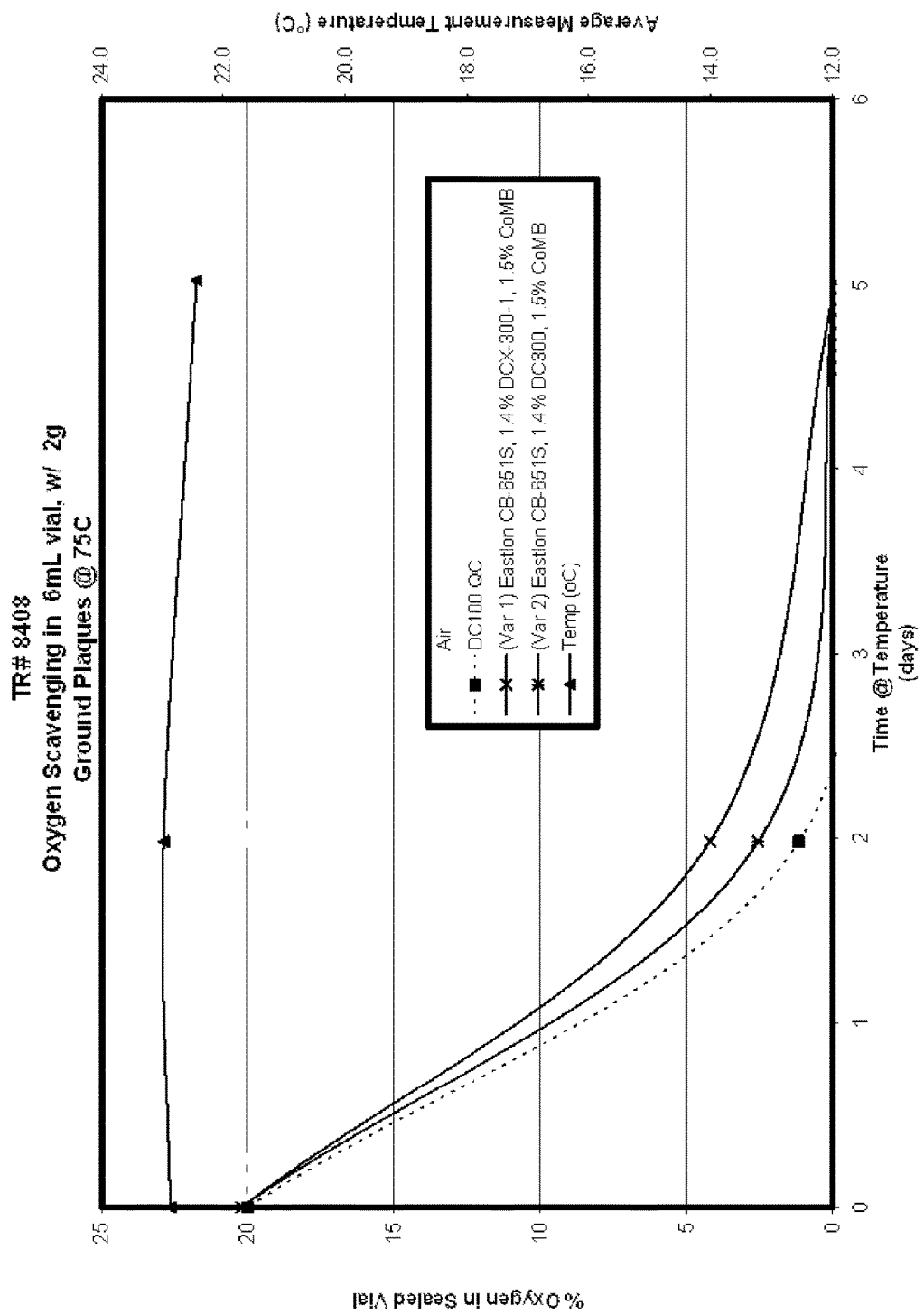
FIG. 2 is a plot showing oxygen scavenging ability of a disclosed composition.

Plaques formed from the above composition were collected and tested for oxygen scavenging ability using Oxysense™. The plaques were ground to fine powder, placed in a sealed glass vial, with a photoluminescent window on the wall. The intensity of light reflected from the photoluminescent window is proportional to the oxygen content in the vial. The Oxysense™ data for the above composition, a similar composition comprised of Constar International's DC-300 as the oxygen scavenger, and a control composition comprised of Constar International's DC-100 are shown in FIG. 2. As seen from the data of FIG. 2, the compound 2-benzyl-1-isoindolinone (DCX-300-1) does scavenge oxygen when melt-blended with cobalt catalyst in a PET matrix.

In addition to preparing the disclosed oxygen scavenger encompassed within this aspect, the formulator can purchase the compounds from one or more suppliers when available. The compounds can also be formed in situ. For example, the addition of 2,2'-[1,3-pehenylenebis(methylene)]diisoindolin-1-one having the formula:

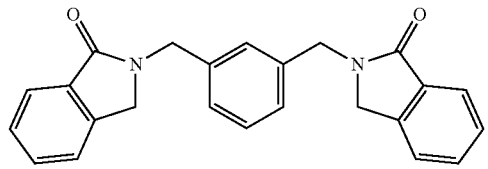 [SMILES: O=C1c2ccccc2CN1Cc1cccc(CN2Cc3ccccc3C2=O)c1]

to the thermoplastic polymers disclosed herein will result in the formation of 2-methylisoindolin-1-one in the final melt composition.

For mixtures of lower molecular weight oxygen scavengers desired by the formulator, a compound such as 6,7-dimethoxy-2-{3-[(1-oxoisoindolin-2-yl)methyl]-benzylisoindolin-1-one having the formula:

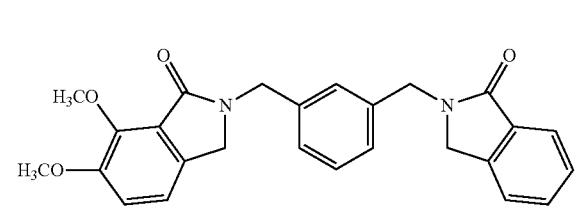 [SMILES: COc1ccc2c(c1OC)C(=O)N(Cc1cccc(CN3Cc4ccccc4C3=O)c1)C2]

can be added to the thermoplastic polymer wherein the resulting melt will comprise both 2-methylisoindolin-1-one and 6,7-dimethoxy-2-methylisoindolin-1-one having the respective formulae:

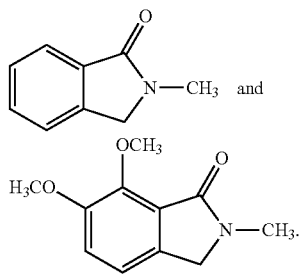

Oxygen scavengers such as 6,7-dimethoxy-2-{3-[(1-oxoisoindolin-2-yl)methyl]-benzylisoindolin-1-one and 6,7-dimethoxy-2-{3-[(1-oxoisoindolin-2-yl)methyl]-benzylisoindolin-1-one can be prepared by the procedures outlined and disclosed in U.S. Patent Application Publication 2008/0277622 A1, the entirety of which is incorporated herein by reference. Modifications to the procedures disclosed in U.S. Patent Application Publication 2008/0277622 A1 to afford the compounds disclosed herein are within the skill of the organic chemist.

Thermoplastic Polymers

Non-limiting examples of suitable thermoplastic polymers that can be used alone or with other polymers include both homopolymers and copolymers, of olefinically unsaturated monomers, for example, polyolefins such as polyethylene, polypropylene, polybutadiene, poly-halohydrocarbons such as polyvinyl chloride, polychloroprene, polyvinylidene chloride, polyfluoro olefins, natural and synthetic rubbers such as copolymers of olefinically unsaturated monomers including styrene-butadiene rubber (SBR rubber), ethylenepropylene copolymers, ethylene-propylenediene terpolymers such as the terpolymer of ethylene, propylene and cyclopentadiene or 1,4-cyclooctadiene, polybutadiene rubbers such as cis-polybutadiene rubber, poly-2-chloro-1,3-butadiene (neoprene) and poly-2-methyl-1,3-butadiene (isoprene rubber), acrylonitrile-butadiene-styrene (ABS) resins, ethylenevinyl acetate copolymers, butene-methylacrylate copolymers, nitrogen-containing polymers such as polyurethanes, nitrile rubber, and lauryl acrylate-vinyl-pyrrolidone copolymers.

Antioxidant Protection by the Disclosed Oxygen Scavengers

The disclosed oxygen scavengers can also protect other compounds and compositions that are susceptible to damage by oxygen. The following are non-limiting examples.

Petroleum oils such as solvent-refined, midcontinent lubricating oil and Gulfcoast lubricating oils are effectively stabilized. In hydrocarbon lubricating oils, both mineral and synthetic, the present additives are particularly effective when used in combination with a zinc dihydrocarbyldithiophosphate, e.g. zinc dialkyldithiophosphate or zinc dialkaryldithiophosphate.

Synthetic ester lubricants such as those used in turbines and turbojet engines are given a high degree of stabilization. Typical synthetic ester lubricants include di-2-ethylhexyl sebacate, trimethylolpropane tripelargonate, $C_5$-$C_9$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethyleneglycol and a mixture of $C_5$-$C_9$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenol using a copper-pyridine catalyst are stabilized. Polycarbonate plastics and other polyformaldehydes are also protected.

Linear polyesters such as phthalic anhydride-glycol condensates are given a high degree of protection. Polyesters such as those derived from terephthalic acid and alkylene glycols are also given a high degree of protection. Other polyesters such as trimellitic acid-glycerol condensates are also protected. Polyacrylates such as polymethylacrylate and polymethylmethacrylate are effectively stabilized. Polyacrylonitriles and copolymers of acrylonitriles with other olefinically unsaturated monomers such as methylmeth-acrylates are also effectively stabilized.

The additives can be used to protect any of the many organic substrates to which an antioxidant is normally added. It can be used where economics permit to protect such substrates as asphalt, paper, fluorocarbons such as Teflon®, polyvinyl acetate, polyvinylidene chloride, coumarone-indene resins, polyvinyl ethers, polyvinylidene bromide, polyvinyl bromide, acrylonitrile, vinyl bromide copolymer, vinyl butyral resins, silicones such as dimethylsilicone lubricants, phosphate lubricants such as tricresylphosphate, and the like.

One embodiment disclosed herein is the incorporation of the disclosed oxygen scavenger into polyethylene terephthalate formulations which further include a transition metal catalyst. The oxygen scavenger works particularly well in the presence of the transition metal catalyst.

In combination with the composition components, compositions disclosed herein can include a transition metal salt, compound or complex, as an oxygen scavenger catalyst. The transition metal can be selected from the first, second, or third transition series of the Periodic Table. The metal can be Rh, Ru, or one of the elements in the series of Sc to Zn (i.e., Sc, Ti, V, Cr, Mn, Fe, Co, Ni, Cu, and Zn). Suitable anions for the salts include, but are not limited to, chloride, acetate, oleate, stearate, palmitate, 2-ethylhexanoate, neodecanoate, and naphthenate. Representative salts include cobalt (II) 2-ethylhexanoate, cobalt oleate, and cobalt (II) neodecanoate. The metal salt also can be an ionomer, in which case a polymeric counter ion can be employed.

The amounts of the components used in the oxygen scavenging formulations of the present disclosure can affect the use and effectiveness of this composition. Thus, the amounts of polymer, transition metal catalyst, antioxidant, polymeric diluents, additives, etc., can vary depending on the desired article and its end use. For example, one of the primary functions of the antioxidant or oxygen scavenging molecules described above is to react irreversibly with oxygen during the scavenging process, while a primary function of the transition metal catalyst is to facilitate this process. Thus, to a large extent, the amount of antioxidant (or oxygen scavenging molecules) present affects the oxygen scavenging capacity of the composition, i.e., the amount of oxygen that the composition can consume, while the amount of transition metal catalyst affects the rate at which oxygen is consumed as well as the induction period.

Methods of incorporating the additive into the substrate are well known. For example, if the substrate is liquid the additive can be merely mixed into the substrate. Frequently the organic substrate is in solution and the additive is added to the solution and the solvent removed. Solid organic substrates can be merely sprayed with a solution of the additive in a volatile solvent. For example, stabilized grain products result from spraying the grain with a toluene solution of the additive. In the case of rubbery polymers the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cispolybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized.

The oxygen scavenger composition of the present disclosure can be incorporated in packaging articles having various forms. Suitable articles include, but are not limited to, flexible sheet films, flexible bags, pouches, semi-rigid and rigid containers such as bottles (e.g. PET bottles) or metal cans, or combinations thereof.

Typical flexible films and bags include those used to package various food items and can be made up of one or a multiplicity of layers to form the overall film or bag-like packaging material. The oxygen scavenger composition of the present disclosure can be used in one, some or all of the layers of such packaging material.

Typical rigid or semi-rigid articles include plastic, paper or cardboard containers, such as those utilized for juices, soft drinks, as well as thermoformed trays or cups normally having thickness in the range of from 100 to 1000 micrometers. The walls of such articles can comprise single or multiple layers of materials. The articles can also take the form of a bottle or metal can, or a crown, cap, crown or cap liner, plastisol or gasket. The oxygen scavenger composition of the present disclosure can be used as an integral layer or portion of, or as an external or internal coating or liner of, the formed semi-rigid or rigid packaging article. As a liner, the oxygen scavenger composition can be extruded as a film along with the rigid article itself, in e.g. a coextrusion, extrusion coating, or extrusion lamination process, so as to form the liner in situ during article production; or alternatively can be adhered by heat and/or pressure, by adhesive, or by any other suitable method to an outer surface of the article after the article has been produced.

Although it can be preferable from the standpoint of packaging convenience and/or scavenging effectiveness to employ the present disclosure as an integral or discrete part of the packaging wall, the disclosure can also be used as a non-integral component of a packaging article such as, for example, a bottle cap liner, adhesive or non-adhesive sheet insert, sealant, sachet, fibrous mat insert or the like.

Besides articles applicable for packaging food and beverage, articles for packaging other oxygen-sensitive products can also benefit from the present disclosure. Such products would include pharmaceuticals, oxygen sensitive medical products, corrodible metals or products, electronic devices and the like.

In some embodiments of the disclosure, the base polymer in the composition is a polyester. In certain embodiments, the polyester polymers of the disclosure are thermoplastic and, thus, the form of the compositions are not limited and can include a composition in the melt phase polymerization, as an amorphous pellet, as a solid stated polymer, as a semi-crystalline particle, as a composition of matter in a melt processing zone, as a bottle preform, or in the form of a stretch blow molded bottle or other articles. In certain preferred embodiments, the polyester is polyethylene terephthalate (PET).

Examples of suitable polyester polymers include polyethylene terephthalate homopolymers and copolymers modified with one or more polycarboxylic acid modifiers in a cumulative amount of less than about 15 mole %, or about 10 mole % or less, or about 8 mole % or less, or one or more hydroxyl compound modifiers in an amount of less than about 60 mol %, or less than about 50 mole %, or less than about 40 mole %, or less than about 15 mole %, or about 10 mole % or less, or about 8 mole % or less (collectively referred to for brevity as "PET") and polyethylene naphthalate homopolymers and copolymers modified with a cumulative amount of with less than about 15 mole %, or about 10 mole % or less, or about 8 mole % or less, of one or more polycarboxylic acid modifiers or modified less than about 60 mol %, or less than about 50 mole %, or less than about 40 mole %, or less than about 15 mole %, or about 10 mole % or less, or about 8 mole % or less of one or more hydroxyl compound modifiers (collectively referred to herein as "PEN"), and blends of PET and PEN. A modifier polycarboxylic acid compound or hydroxyl compound is a compound other than the compound contained in an amount of at least about 85 mole %. The preferred polyester polymer is polyalkylene terephthalate, and most preferred is PET.

In some embodiments, the polyester polymer contains at least about 90 mole % ethylene terephthalate repeat units, and in other embodiments, at least about 92 mole %, and in yet other embodiments, at least about 94 mole %, based on the moles of all repeat units in the polyester polymers.

In addition to a diacid component of terephthalic acid, derivates of terephthalic acid, naphthalene-2,6-dicarboxylic acid, derivatives of naphthalene-2,6-dicarboxylic acid, or mixtures thereof, the polycarboxylic acid component(s) of the present polyester can include one or more additional modifier polycarboxylic acids. Such additional modifier polycarboxylic acids include aromatic dicarboxylic acids preferably having about 8 to about 14 carbon atoms, aliphatic dicarboxylic acids preferably having about 4 to about 12 carbon atoms, or cycloaliphatic dicarboxylic acids preferably having about 8 to about 12 carbon atoms. Examples of modifier dicarboxylic acids useful as an acid component(s) are phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like, with isophthalic acid, naphthalene-2,6-dicarboxylic acid, and cyclohexanedicarboxylic acid being most preferable. It should be understood that use of the corresponding acid anhydrides, esters, and acid chlorides of these acids is included in the term "polycarboxylic acid." It is also possible for trifunctional and higher order polycarboxylic acids to modify the polyester.

The hydroxyl component is made from compounds containing 2 or more hydroxyl groups capable of reacting with a carboxylic acid group. In some preferred embodiments, preferred hydroxyl compounds contain 2 or 3 hydroxyl groups. Certain preferred embodiments, have 2 hydroxyl groups. These hydroxyl compounds include $C_2$-$C_4$ alkane diols, such as ethylene glycol, propane diol, and butane diol, among which ethylene glycol is most preferred for container applications. In addition to these diols, other modifier hydroxyl compound component(s) can include diols such as cycloaliphatic diols preferably having 6 to 20 carbon atoms and/or aliphatic diols preferably having about 3 to about 20 carbon atoms. Examples of such diols include diethylene glycol; triethylene glycol; 1,4-cyclohexanedimethanol; propane-1,3-diol and butane-1,4-diol (which are considered modifier diols if ethylene glycol residues are present in the polymer in an amount of at least 85 mole % based on the moles of all hydroxyl compound residues); pentane-1,5-diol; hexane-1,6-diol; 3-methylpentanediol-(2,4); neopentyl glycol; 2-methylpentanediol-(1,4); 2,2,4-trimethylpentanediol-(1,3); 2,5-ethylhexanediol-(1,3); 2,2-diethyl propanediol-(1,3); hexanediol-(1,3); 1,4-di-(hydroxyethoxy)-benzene; 2,2-bis-(4-hydroxycyclohexyl)-propane; 2,4-dihydroxy-1,1,3,3-tetramethyl-cyclobutane; 2,2-bis-(3-hydroxyethoxyphenyl)-propane; and 2,2-bis-(4-hydroxypropoxyphenyl)-propane. Typically, polyesters such as polyethylene terephthalate are made by reacting a glycol with a dicarboxylic acid as the free acid or its dimethyl ester to produce an ester monomer and/or oligomers, which are then polycondensed to produce the polyester.

In some preferred embodiments, modifiers include isophthalic acid, naphthalenic dicarboxylic acid, trimellitic anhydride, pyromellitic dianhydride, 1,4-cyclohexane dimethanol, and diethylene glycol. The amount of the polyester polymer in the formulated polyester polymer composition ranges from greater than about 50.0 wt. %, or from about 80.0 wt. %, or from about 90.0 wt. %, or from about 95.0 wt. %, or from about 96.0 wt. %, or from about 97 wt. %, and up to about 99.90 wt. %, based on the combined weight of all polyester polymers and all polyamide polymers. The formulated polyester polymer compositions can also include blends of formulated polyester polymer compositions with other thermoplastic polymers such as polycarbonate. In some preferred compositions, the polyester comprises a majority of the composition of the disclosures, and in some embodiments the polyester is present in an amount of at least about 80 wt. %, or at least about 90 wt. %, based on the weight of the composition (excluding fillers, inorganic compounds or particles, fibers, impact modifiers, or other polymers serve as impact modifiers or which form a discontinuous phase such as can be found in cold storage food trays).

The polyester compositions can be prepared by polymerization procedures known in the art sufficient to effect esterification and polycondensation. Polyester melt phase manufacturing processes include direct condensation of a dicarboxylic acid with the diol, optionally in the presence of esterification catalysts, in the esterification zone, followed by polycondensation in the prepolymer and finishing zones in the presence of a polycondensation catalyst; or ester exchange usually in the presence of a transesterification catalyst in the ester exchange zone, followed by prepolymerization and finishing in the presence of a polycondensation catalyst, and each can optionally be solid stated according to known methods.

The transition metal used in the instant compositions is a metal in the positive oxidation state. It should be noted that it is contemplated that one or more such metals can be used. In some embodiments, cobalt is added in +2 or +3 oxidation state. In some embodiments, it is preferred to use cobalt in the +2 oxidation state. In certain embodiments, copper in the +2 oxidation state is utilized. In some embodiments, rhodium in the +2 oxidation state is used. In certain embodiments, zinc can also be added to the composition. Preferred zinc compounds include those in a positive oxidation state.

Suitable counter-ions to the transition metal cations include carboxylates, such as neodecanoates, octanoates, acetates, lactates, naphthalates, malates, stearates, acetylacetonates, linoleates, oleates, palmitates, 2-ethylhexanoates, or ethylene glycolates; or as their oxides, borates, carbonates, chlorides, dioxides, hydroxides, nitrates, phosphates, sulfates, or silicates among others.

In some embodiments, levels of at least about 10 ppm, or at least about 50 ppm, or at least about 100 ppm of metal can achieve suitable oxygen scavenging levels. The exact amount of transition metal used in an application can be determined by trials that are well within the skill level of one skilled in the art. In some embodiments involving wall applications (as opposed to master batch applications where more catalyst is used), it is preferred to keep the level of metal below about 300 ppm and, in other embodiments, preferably below about 250 ppm.

The transition metal or metals can be added neat or in a carrier (such as a liquid or wax) to an extruder or other device for making the article, or the metal can be present in a concentrate or carrier with the oxidizable organic component, in a concentrate or carrier with a base polymer, or in a concentrate or carrier with a base polymer/oxidizable organic component blend. Alternatively, at least a portion of the transition metal can be added as a polymerization catalyst to the melt phase reaction for making the base polymer (a polyester polymer in some embodiments) and be present as residual metals when the polymer is fed to the melting zone (e.g. the extrusion or injection molding zone) for making the article such as a preform or sheet. It is desirable that the addition of the transition metal does not substantially increase the intrinsic viscosity (I.V.) of the melt in the melt processing zone. Thus, transition metal or metals can be added in two or more stages, such as once during the melt phase for the production of the polyester polymer and again once more to the melting zone for making the article.

The composition can also include other components such as colorants, pigments, fillers, crystallization aids, impact modifiers, surface lubricants, denesting agents, stabilizers, ultraviolet light absorbing agents, metal deactivators, nucleating agents such as polyethylene and polypropylene, phosphate stabilizers and dyestuffs. Other additional components are well known to those skilled in the art and can be added to the existing composition so long as they do not negatively impact the performance of the compositions. Typically, the total quantity of such components will be less than about 10% by weight relative to the whole composition. In some embodiments, the amount of these optional components is less than about 5%, by weight relative to the total composition.

A common additive used in the manufacture of polyester polymer compositions used to make stretch blow molded bottles is a reheat additive because the preforms made from the composition must be reheated prior to entering the mold for stretch blowing into a bottle. Any of the conventional reheat additives can be used, such additives include various forms of black particles, e.g. carbon black, activated carbon, black iron oxide, glassy carbon, and silicon carbide; the gray particles such as antimony, and other reheat additives such as silicas, red iron oxide, and so forth.

Other typical additives, depending on the application, are impact modifiers. Examples of typical commercially available impact modifiers well-known in the art and useful in this disclosure include ethylene/acrylate/glycidyl terpolymers and ethylene/acrylate copolymers in which the acrylate is a methyl or ethyl acrylate or methyl or ethyl methacrylate or the corresponding butyl acrylates, styrene based block copolymers, and various acrylic core/shell type impact modifiers. The impact modifiers can be used in conventional amounts from about 0.1 to about 25 weight percent of the overall composition and, in some embodiments, preferably in amounts from about 0.1 to about 10 weight percent of the composition.

In many applications, not only are the packaging contents sensitive to the ingress of oxygen, but the contents can also be affected by UV light. Fruit juices and pharmaceuticals are two examples of such contents. Accordingly, in some embodiments, it is desirable to incorporate into the polyester composition any one of the known UV absorbing compounds in amounts effective to protect the packaged contents.

The instant compositions can be made by mixing a base polymer (PET, for example) with the oxidizable organic component and the transition metal composition. Such compositions can be made by any method known to those skilled in the art. In certain embodiments, some or part of the transition metal can exist in the base polymer prior to mixing. This residual metal, for example, can exist from the manufacturing process of the base polymer. In some embodiments, the base polymer, the oxidizable organic component and the transition metal are mixed by tumbling in a hopper. Other optional ingredients can be added during this mixing process or added to the mixture after the aforementioned mixing or to an individual component prior to the aforementioned mixing step.

The instant composition can also be made by adding each ingredient separately and mixing the ingredients prior melt processing the composition to form an article. In some embodiments, the mixing can be just prior to the melt process zone. In other embodiments, one or more ingredients can be premixed in a separate step prior to bringing all of the ingredients together.

In some embodiments, the disclosure concerns use of the compositions described herein as a component of a wall that is used in a package for oxygen sensitive materials. The necessary scavenging capacity of a package will generally have to be greater for walls that have a greater permeance in the absence of scavenging additives. Accordingly, a good effect is harder to achieve with inherently higher permeance materials are used.

The wall can be a rigid one, a flexible sheet, or a clinging film. It can be homogenous or a laminate or coated with other polymers. If it is laminated or coated, then the scavenging property can reside in a layer of the wall the permeance of which is relatively high in the absence of scavenging and which alone would not perform very satisfactorily but which performs satisfactorily in combination with one or more other layers which have a relatively low permeance but negligible or insufficient oxygen-scavenging properties. A single such layer could be used on the outside of the package since this is the side from which oxygen primarily comes when the package is filled and sealed. However, such a layer to either side of the scavenging layer would reduce consumption of scavenging capacity prior to filling and sealing.

When the instant compositions are used in a wall or as a layer of a wall, the permeability of the composition for oxygen is advantageously not more than about 3.0, or about 1.7, or about 0.7, or about 0.2, or about 0.03 $cm^3$ $mm/(m^2$ atm day). The permeability of the composition provided by the present disclosure is advantageously not more than about three-quarters of that in the absence of oxygen-scavenging properties. In some embodiments, the permeability is not more than about one half, one-tenth in certain embodiments, one twenty-fifth in other embodiments, and not more than one-hundredth in yet other embodiments of that in the absence of oxygen-scavenging properties. The permeability in the absence of oxygen-scavenging properties is advantageously not more than about 17 $cm^3$ $mm/(m^2$ atm day), or about 10, and or about 6. A particularly good effect can be achieved for such permeabilities in the range from about 0.5, or about 1.0, to 10, or about 6.0, $cm^3$ $mm/(m^2$ atm day). Measurements of oxygen permeation can be made by methods described, for example, in U.S. Pat. No. 5,639,815, the contents of which are incorporated herein in its entirety.

In another aspect, the instant composition can be used as a master batch for blending with a polymer or a polymer containing component. In such compositions, the concentration of the oxidizable organic component and the transition metal will be higher to allow for the final blended product to have suitable amounts of these components. The master batch can also contain an amount of the polymer to which the master batch is to be blended with. In other embodiments, the master batch can contain a polymer that is compatible with the polymer that the master batch is to be blended with.

In yet another aspect, the compositions of the instant disclosure can be used for forming a layer of a wall which primarily provides oxygen-scavenging (another layer including polymer providing gas barrier without significant scavenging), or as a head-space scavenger (completely enclosed, together with the package contents, by a package wall). Such techniques are well know to those skilled in the art. Persons familiar with oxygen scavenging technology and products will understand how to implement the structures disclosed in this paragraph.

The time period for which the permeability is maintained can be extended by storing the articles in sealed containers or under an inert atmosphere such as nitrogen prior to use with oxygen sensitive materials.

In another aspect, the disclosure provides a package, whether rigid, semi-rigid, collapsible, lidded, or flexible or a combination of these, comprising a wall as formed from the compositions described herein. Such packages can be formed by methods well known to those skilled in the art.

Among the techniques that can be used to make articles are moulding generally, injection moulding, stretch blow moulding, extrusion, thermoforming, extrusion blow moulding, and (specifically for multilayer structures) co-extrusion and lamination using adhesive tie layers. Orientation, e.g. by stretch blow moulding, of the polymer is especially attractive with phthalate polyesters because of the known mechanical advantages that result.

The melt processing zone for making the article can be operated under customary conditions effective for making the intended articles, such as preforms, bottles, trays, and other articles mentioned below. In one embodiment, such conditions are effective to process the melt without substantially increasing the I.V. of the melt and which are ineffective to promote transesterification reactions. In some preferred embodiments, suitable operating conditions effective to establish a physical blend of the polyester polymer, oxidizable organic component, and transition metal are temperatures in the melt processing zone within a range of about 250° C. to about 300° C. at a total cycle time of less than about 6 minutes, and typically without the application of vacuum and under a positive pressure ranging from about 0 psig to about 900 psig. In some embodiments, the residence time of the melt on the screw can range from about 1 to about 4 minutes.

Specific articles include preforms, containers and films for packaging of food, beverages, cosmetics, pharmaceuticals, and personal care products where a high oxygen barrier is needed. Examples of beverage containers are bottles for holding water and carbonated soft drinks, and the disclosure is particularly useful in bottle applications containing juices, sport drinks, beer or any other beverage where oxygen detrimentally affects the flavor, fragrance, performance (prevent vitamin degradation), or color of the drink. The compositions of the instant disclosure are also particularly useful as a sheet for thermoforming into rigid packages and films for flexible structures. Rigid packages include food trays and lids. Examples of food tray applications include dual ovenable food trays, or cold storage food trays, both in the base container and in the lidding (whether a thermoformed lid or a film), where the freshness of the food contents can decay with the ingress of oxygen. The compositions of the instant disclosure also find use in the manufacture of cosmetic containers and containers for pharmaceuticals or medical devices.

The package walls of the instant disclosure can be a single layer or a multilayer constructions. In some embodiments using multilayer walls, the outer and inner layers can be structural layers with one or more protective layers containing the oxygen scavenging material positioned there between. In some embodiments, the outer and inner layers comprise and polyolefin or a polyester. In certain embodiments, a single layer design is preferred. Such a layer can have advantages in simplicity of manufacture and cost.

Unless otherwise indicated, the disclosure is not limited to specific molecular structures, substituents, synthetic methods, reaction conditions, or the like, as such can vary. It is also to be understood that the terminology used herein is for the purpose of describing particular embodiments only and is not intended to be limiting.

What is claimed is:

1. A method for making an oxygen scavenging polymer composition comprising the step of combining:
   a) a thermoplastic polymer;
   b) a transition metal in a positive oxidation state, the metal present in the composition in an amount of from about 10 ppm to about 400 ppm; and
   c) a compound having the formula:

i)

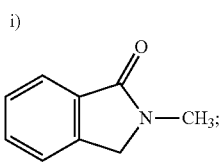

ii)

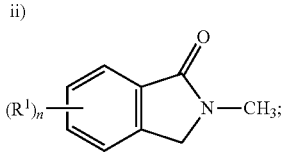

iii)

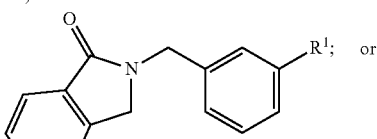

iv)

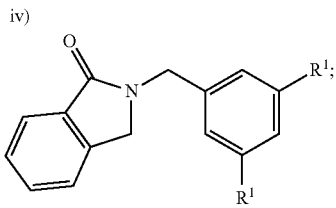

wherein R¹ is chosen from:
   i) —CH₃;
   ii) —CHO; or
   ii) a combination thereof; and
   the index n is equal to 1 or 2.

2. A method of preparing an article comprising the step of providing a polymer composition, the composition comprising:
   a) a thermoplastic polymer;
   b) a transition metal in a positive oxidation state, the metal present in the composition in an amount of from about 10 ppm to about 400 ppm; and
   c) a compound having the formula:

i)

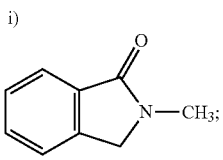

ii)

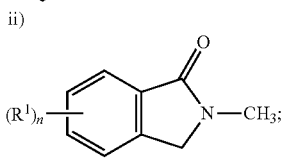

iii)

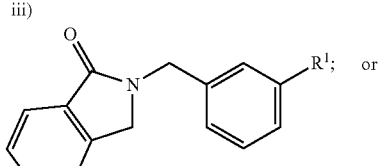

iv)

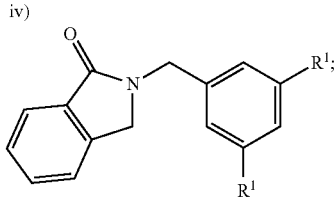

wherein R¹ is chosen from:
   i) —CH₃;
   ii) —CHO; or
   ii) a combination thereof; and
   the index n is equal to 1 or 2, and
   forming an article from the composition.

3. The method of claim 2, wherein the step of forming comprises injection moulding, stretch blow moulding, extrusion, thermoforming, or extrusion blow moulding.

4. The method of claim 2, wherein the step of forming is sheet or film extrusion.

5. The method of claim 2, wherein the article is a bottle or a preform.

6. The method of claim 1, wherein the transition metal is present in the composition in an amount of from about 30 ppm to about 150 ppm.

7. The method of claim 1, wherein the thermoplastic polymer is a polyester homopolymer or polyester copolymer.

8. The method of claim 1, wherein the thermoplastic polymer comprises polyethylene terephthalate or a copolymer thereof.

9. The method of claim 1, wherein the compound comprises from about 1% to about 10% by weight of the composition.

10. The method of claim 1, wherein the compound comprises from about 1% to about 5% by weight of the composition.

11. The method of claim 1, wherein the compound comprises from about 1% to about 3% by weight of the composition.

12. The method of claim 1, further comprising the step of combining a colorant.

13. The method of claim 2, wherein the transition metal is present in the composition in an amount of from about 30 ppm to about 150 ppm.

14. The method of claim 2, wherein the thermoplastic polymer is a polyester homopolymer or polyester copolymer.

15. The method of claim 2, wherein the thermoplastic polymer comprises polyethylene terephthalate or a copolymer thereof.

16. The method of claim 2, wherein the compound comprises from about 1% to about 10% by weight of the composition.

17. The method of claim 2, wherein the compound comprises from about 1% to about 5% by weight of the composition.

18. The method of claim 2, wherein the compound comprises from about 1% to about 3% by weight of the composition.

19. The method of claim 2, further comprising the step of combining a colorant.

20. The method of claim 2, wherein the article is a sheet, a cup, or a jar.

* * * * *